(12) United States Patent
Duerr et al.

(10) Patent No.: US 9,676,684 B2
(45) Date of Patent: *Jun. 13, 2017

(54) PROCESS AND UNIT FOR SOLVENT RECOVERY FROM SOLVENT DILUTED TAILINGS DERIVED FROM BITUMEN FROTH TREATMENT

(75) Inventors: Ryan Duerr, Calgary (CA); Shawn Van Der Merwe, Calgary (CA); Tom Hann, Onoway (CA)

(73) Assignee: FORT HILLS ENERGY L.P., Calgary (CA)

( * ) Notice: Subject to any disclaimer, the term of this patent is extended or adjusted under 35 U.S.C. 154(b) by 357 days.

This patent is subject to a terminal disclaimer.

(21) Appl. No.: 14/002,630

(22) PCT Filed: Feb. 23, 2012

(86) PCT No.: PCT/CA2012/050108
§ 371 (c)(1),
(2), (4) Date: Aug. 30, 2013

(87) PCT Pub. No.: WO2012/116442
PCT Pub. Date: Sep. 7, 2012

(65) Prior Publication Data
US 2013/0345485 A1  Dec. 26, 2013

(30) Foreign Application Priority Data
Mar. 1, 2011 (CA) ..................... 2733342

(51) Int. Cl.
*C07C 7/11* (2006.01)
*C10G 1/04* (2006.01)

(52) U.S. Cl.
CPC .................. *C07C 7/11* (2013.01); *C10G 1/04* (2013.01); *C10G 1/045* (2013.01); *C10G 2300/4081* (2013.01); *C10G 2300/44* (2013.01)

(58) Field of Classification Search
None
See application file for complete search history.

(56) References Cited

U.S. PATENT DOCUMENTS

| 181,668 A | 8/1876 | Gregg et al. |
|---|---|---|
| 654,965 A | 7/1900 | Franke |
| (Continued) | | |

FOREIGN PATENT DOCUMENTS

| CA | 918091 A1 | 1/1973 |
|---|---|---|
| CA | 918588 A1 | 1/1973 |
| (Continued) | | |

OTHER PUBLICATIONS

Bui et al., "Modelling of Viscous Resuspension Using a One-Field Description of Multiphase Flows", Third International Conference on CFD in the Minerals and Process Industries, 2003 pp. 265-268.
(Continued)

*Primary Examiner* — Tam M Nguyen
(74) *Attorney, Agent, or Firm* — Marshall, Gerstein & Borun LLP

(57) ABSTRACT

A TSRU for recovering solvent from solvent diluted tailings includes a separation apparatus receiving the tailings and producing solvent and solvent recovered tailings. The separation apparatus includes a vessel, a tailings outlet, a solvent outlet, a tailings inlet for supplying a variable flow of the tailings to the vessel and a tailings recycle line connected to the tailings inlet for recycling part of the solvent recovered tailings into the variable flow of the diluted tailings to produce a flow rate controlled feed for introduction into the vessel. A tailings solvent recovery process includes separating the diluted tailings into recovered solvent and solvent recovered tailings, discharging the solvent recovered tailings, and recycling a portion of the solvent recovered tailings back into the variable flow of the diluted tailings. A
(Continued)

method of controlling feed flow rate to a tailings solvent recovery vessel is also provided.

74 Claims, 3 Drawing Sheets

(56) References Cited

U.S. PATENT DOCUMENTS

| | | |
|---|---|---|
| 1,085,135 A | 1/1914 | Kelly, Jr. |
| 1,147,356 A | 7/1915 | Allen |
| 1,159,044 A | 11/1915 | Kelly, Jr. |
| 1,201,558 A | 10/1916 | Cobb |
| 1,254,562 A | 1/1918 | Allen |
| 1,261,671 A | 4/1918 | Zachert |
| 1,494,375 A | 5/1924 | Reilly |
| 1,754,119 A | 4/1930 | Pink |
| 1,777,535 A | 10/1930 | Walcott Stratford |
| 2,010,008 A | 8/1935 | Bray |
| 2,047,989 A | 7/1936 | William |
| 2,091,078 A | 8/1937 | McKittrick et al. |
| 2,111,717 A | 3/1938 | Young |
| 2,188,013 A | 1/1940 | Pilat et al. |
| 2,240,008 A | 4/1941 | Atwell |
| 2,410,483 A | 11/1946 | Dons et al. |
| 2,853,426 A | 9/1958 | Peet |
| 2,868,714 A | 1/1959 | Gilmore |
| 3,081,823 A | 3/1963 | Constantikes |
| 3,220,193 A | 11/1965 | Sttohmeyer, Jr. |
| 3,271,293 A | 9/1966 | Clark |
| 3,278,415 A | 10/1966 | Doberenz et al. |
| 3,291,569 A | 12/1966 | Joseph Rossi |
| 3,575,842 A | 4/1971 | Simpson |
| 3,705,491 A | 12/1972 | Foster-Pegg |
| 3,779,902 A | 12/1973 | Mitchell et al. |
| 3,808,120 A | 4/1974 | Smith |
| 3,901,791 A | 8/1975 | Baillie |
| 3,929,625 A | 12/1975 | Lucas |
| 3,954,414 A | 5/1976 | Samson, Jr. et al. |
| 3,957,655 A | 5/1976 | Barefoot |
| 4,013,542 A | 3/1977 | Gudelis et al. |
| 4,035,282 A | 7/1977 | Stuchberry et al. |
| 4,115,241 A | 9/1978 | Harrison et al. |
| 4,116,809 A | 9/1978 | Kizior |
| 4,120,775 A | 10/1978 | Murray et al. |
| 4,140,620 A | 2/1979 | Paulett |
| 4,209,422 A | 6/1980 | Zimmerman et al. |
| 4,210,820 A | 7/1980 | Wittig |
| 4,230,467 A | 10/1980 | Buchwald |
| 4,251,627 A | 2/1981 | Calamur |
| 4,284,242 A | 8/1981 | Randell |
| 4,314,974 A | 2/1982 | Libby et al. |
| 4,315,815 A | 2/1982 | Gearhart |
| 4,321,147 A | 3/1982 | McCoy et al. |
| 4,324,652 A | 4/1982 | Hack |
| 4,342,657 A | 8/1982 | Blair |
| 4,346,560 A | 8/1982 | Rapier |
| 4,395,330 A | 7/1983 | Auboir et al. |
| 4,410,417 A | 10/1983 | Miller et al. |
| 4,425,227 A | 1/1984 | Smith |
| 4,461,696 A | 7/1984 | Bock et al. |
| 4,470,899 A | 9/1984 | Miller et al. |
| 4,495,057 A | 1/1985 | Amirijafari et al. |
| 4,514,305 A | 4/1985 | Filby |
| 4,518,479 A | 5/1985 | Schweigharett et al. |
| 4,532,024 A | 7/1985 | Haschke et al. |
| 4,539,093 A | 9/1985 | Friedman et al. |
| 4,545,892 A | 10/1985 | Cymbalisty et al. |
| 4,572,781 A | 2/1986 | Krasuk et al. |
| 4,584,087 A | 4/1986 | Peck |
| 4,609,455 A | 9/1986 | Weimer et al. |
| 4,634,520 A | 1/1987 | Angelov et al. |
| 4,640,767 A | 2/1987 | Zajic et al. |
| 4,644,974 A | 2/1987 | Zingg |
| 4,648,964 A | 3/1987 | Leto et al. |
| 4,678,558 A | 7/1987 | Belluteau et al. |
| 4,722,782 A | 2/1988 | Graham et al. |
| 4,726,759 A | 2/1988 | Wegener |
| 4,781,819 A | 11/1988 | Chirinos et al. |
| 4,802,975 A | 2/1989 | Mehlberg |
| 4,822,481 A | 4/1989 | Taylor |
| 4,828,688 A | 5/1989 | Corti et al. |
| 4,859,317 A | 8/1989 | Shelfantook et al. |
| 4,888,108 A | 12/1989 | Farnand |
| 4,906,355 A | 3/1990 | Lechnick et al. |
| 4,929,341 A | 5/1990 | Thirumalachar et al. |
| 4,931,072 A | 6/1990 | Striedieck |
| 4,950,363 A | 8/1990 | Silvey |
| 4,966,685 A | 10/1990 | Hall et al. |
| 4,968,413 A | 11/1990 | Datta et al. |
| 5,022,983 A | 6/1991 | Myers et al. |
| 5,039,227 A | 8/1991 | Leung et al. |
| 5,133,837 A | 7/1992 | Elmore |
| 5,143,598 A | 9/1992 | Graham et al. |
| 5,186,820 A | 2/1993 | Schultz et al. |
| 5,223,148 A | 6/1993 | Tipman et al. |
| 5,236,577 A | 8/1993 | Tipman |
| 5,264,118 A | 11/1993 | Cymerman et al. |
| 5,282,984 A | 2/1994 | Ashrawi |
| 5,298,167 A | 3/1994 | Arnold |
| 5,443,046 A | 8/1995 | White |
| 5,558,768 A | 9/1996 | Ikura et al. |
| 5,645,714 A | 7/1997 | Strand et al. |
| 5,690,811 A | 11/1997 | Davis et al. |
| 5,817,398 A | 10/1998 | Hollander |
| 5,871,634 A | 2/1999 | Wiehe et al. |
| 5,876,592 A | 3/1999 | Tipman et al. |
| 5,879,540 A | 3/1999 | Zinke et al. |
| 5,914,010 A | 6/1999 | Hood et al. |
| 5,937,817 A | 8/1999 | Schanz et al. |
| 5,948,241 A | 9/1999 | Owen |
| 5,954,277 A | 9/1999 | Maciejewski et al. |
| 5,968,349 A | 10/1999 | Duyvesteyn et al. |
| 5,985,138 A | 11/1999 | Humphreys |
| 5,988,198 A | 11/1999 | Neiman et al. |
| 5,997,723 A | 12/1999 | Wiehe et al. |
| 6,004,455 A | 12/1999 | Rendall |
| 6,007,708 A | 12/1999 | Allcock et al. |
| 6,007,709 A | 12/1999 | Duyvesteyn et al. |
| 6,019,888 A | 2/2000 | Mishra et al. |
| 6,036,748 A | 3/2000 | Wallace et al. |
| 6,076,753 A | 6/2000 | Maciejewski et al. |
| 6,110,359 A | 8/2000 | Davis et al. |
| 6,120,678 A | 9/2000 | Stephenson et al. |
| 6,159,442 A | 12/2000 | Thumm et al. |
| 6,214,213 B1 | 4/2001 | Tipman et al. |
| 6,355,159 B1 | 3/2002 | Myers et al. |
| 6,358,403 B1 | 3/2002 | Brown et al. |
| 6,361,025 B1 | 3/2002 | Cincotta et al. |
| 6,391,190 B1 | 5/2002 | Spence et al. |
| 6,482,250 B1 | 11/2002 | Williams et al. |
| 6,497,813 B2 | 12/2002 | Ackerson et al. |
| 6,523,573 B2 | 2/2003 | Robison et al. |
| 6,566,410 B1 | 5/2003 | Zaki et al. |
| 6,746,599 B2 | 6/2004 | Cymerman et al. |
| 6,800,116 B2 | 10/2004 | Stevens et al. |
| 7,152,851 B2 | 12/2006 | Cincotta |
| 7,357,857 B2 | 4/2008 | Hart et al. |
| 7,569,137 B2 | 8/2009 | Hyndman |
| 7,690,445 B2 | 4/2010 | Perez-Cordova |
| 7,749,378 B2 | 7/2010 | Iqbal et al. |
| 7,820,031 B2 | 10/2010 | D'Alessandro et al. |
| 7,909,989 B2 | 3/2011 | Duyvesteyn et al. |
| 7,934,549 B2 | 5/2011 | Cimolai |
| 8,133,316 B2 | 3/2012 | Poncelet et al. |
| 8,141,636 B2 | 3/2012 | Speirs et al. |
| 8,147,682 B2 | 4/2012 | Lahaie et al. |
| 8,157,003 B2 | 4/2012 | Hackett et al. |
| 8,252,107 B2 | 8/2012 | Esmaeili et al. |
| 8,261,831 B2 | 9/2012 | Lockhart et al. |
| 8,262,865 B2 | 9/2012 | Sharma et al. |
| 8,312,928 B2 | 11/2012 | Lockhart et al. |
| 8,343,337 B2 | 1/2013 | Moffett et al. |
| 8,354,020 B2 | 1/2013 | Sharma et al. |
| 8,357,291 B2 | 1/2013 | Sury et al. |

(56) References Cited

U.S. PATENT DOCUMENTS

| | | |
|---|---|---|
| 8,382,976 B2 | 2/2013 | Moran et al. |
| 8,394,180 B2 | 3/2013 | Diaz et al. |
| 8,449,764 B2 | 5/2013 | Chakrabarty et al. |
| 8,454,821 B2 | 6/2013 | Chakrabarty et al. |
| 8,455,405 B2 | 6/2013 | Chakrabarty |
| 8,550,258 B2 | 10/2013 | Bara et al. |
| 8,585,891 B2 | 11/2013 | Lourenco et al. |
| 2002/0043579 A1 | 4/2002 | Scheybeler |
| 2003/0089636 A1 | 5/2003 | Marchionna et al. |
| 2004/0074845 A1 | 4/2004 | Hagino et al. |
| 2004/0256325 A1 | 12/2004 | Frankiewicz |
| 2005/0150816 A1 | 7/2005 | Gaston |
| 2005/0150844 A1 | 7/2005 | Hyndman et al. |
| 2006/0065869 A1 | 3/2006 | Chipman et al. |
| 2006/0138055 A1 | 6/2006 | Garner et al. |
| 2006/0196812 A1 | 9/2006 | Beetge et al. |
| 2007/0125719 A1 | 6/2007 | Yarbrough |
| 2007/0180741 A1 | 8/2007 | Bjornson et al. |
| 2007/0284283 A1 | 12/2007 | Duyvesteyn |
| 2008/0000810 A1 | 1/2008 | Garner et al. |
| 2008/0185350 A1 | 8/2008 | Remesat et al. |
| 2008/0210602 A1 | 9/2008 | Duyvesteyn |
| 2009/0134059 A1 | 5/2009 | Myers et al. |
| 2009/0200210 A1 | 8/2009 | Hommema |
| 2009/0200688 A1 | 8/2009 | Cincotta |
| 2009/0294328 A1 | 12/2009 | Iqbal |
| 2009/0321322 A1 | 12/2009 | Sharma |
| 2009/0321324 A1 | 12/2009 | Sharma |
| 2010/0006474 A1 | 1/2010 | Gaston et al. |
| 2010/0076236 A1 | 3/2010 | Van Heuzen et al. |
| 2010/0078306 A1 | 4/2010 | Alhazmy |
| 2010/0089800 A1 | 4/2010 | MacDonald et al. |
| 2010/0096297 A1 | 4/2010 | Stevens et al. |
| 2010/0126395 A1 | 5/2010 | Gauthier |
| 2010/0126906 A1 | 5/2010 | Sury |
| 2010/0133149 A1 | 6/2010 | O'Connor et al. |
| 2010/0147516 A1 | 6/2010 | Betzer-Zilevitch |
| 2010/0155293 A1 | 6/2010 | Verstraete et al. |
| 2010/0155304 A1 | 6/2010 | Ding et al. |
| 2010/0206772 A1 | 8/2010 | Keppers |
| 2010/0243534 A1 | 9/2010 | Ng et al. |
| 2010/0258477 A1 | 10/2010 | Kukkonen et al. |
| 2010/0258478 A1 | 10/2010 | Moran et al. |
| 2010/0264068 A1 | 10/2010 | Ikebe et al. |
| 2010/0276341 A1 | 11/2010 | Speirs et al. |
| 2010/0276983 A1 | 11/2010 | Dunn et al. |
| 2010/0282642 A1 | 11/2010 | Kan |
| 2010/0298173 A1 | 11/2010 | Smith et al. |
| 2010/0320133 A1 | 12/2010 | Page et al. |
| 2011/0005750 A1 | 1/2011 | Boerseth et al. |
| 2011/0011769 A1 | 1/2011 | Sutton et al. |
| 2011/0061610 A1 | 3/2011 | Speirs et al. |
| 2011/0062090 A1 | 3/2011 | Bara |
| 2011/0089013 A1 | 4/2011 | Sakurai et al. |
| 2011/0100931 A1 | 5/2011 | Lake et al. |
| 2011/0127197 A1 | 6/2011 | Blackbourn et al. |
| 2011/0146164 A1 | 6/2011 | Haney et al. |
| 2011/0174683 A1 | 7/2011 | Cui et al. |
| 2011/0219680 A1 | 9/2011 | Wilkomirsky Fuica |
| 2011/0233115 A1 | 9/2011 | Moran et al. |
| 2011/0265558 A1 | 11/2011 | Feimer et al. |
| 2011/0284428 A1 | 11/2011 | Adeyinka et al. |
| 2012/0000830 A1 | 1/2012 | Monaghan et al. |
| 2012/0000831 A1 | 1/2012 | Moran et al. |
| 2012/0029259 A1 | 2/2012 | McFarlane et al. |
| 2012/0043178 A1 | 2/2012 | Kan |
| 2012/0074044 A1 | 3/2012 | McFarlane |
| 2012/0074045 A1 | 3/2012 | Stauffer et al. |
| 2012/0145604 A1 | 6/2012 | Wen |
| 2012/0175315 A1 | 7/2012 | Revington et al. |
| 2012/0217187 A1 | 8/2012 | Sharma et al. |
| 2012/0288419 A1 | 11/2012 | Esmaeili et al. |
| 2013/0043165 A1 | 2/2013 | Revington et al. |
| 2013/0081298 A1 | 4/2013 | Bugg et al. |
| 2013/0140249 A1 | 6/2013 | Sury et al. |
| 2013/0168294 A1 | 7/2013 | Chakrabarty et al. |
| 2013/0313886 A1 | 11/2013 | Van Der Merwe et al. |
| 2014/0001101 A1 | 1/2014 | Van Der Merwe et al. |
| 2014/0011147 A1 | 1/2014 | Van Der Merwe |
| 2014/0048408 A1 | 2/2014 | Van Der Merwe et al. |
| 2014/0048450 A1 | 2/2014 | Van Der Merwe et al. |
| 2014/0076785 A1 | 3/2014 | Penner et al. |
| 2014/0083911 A1 | 3/2014 | Van Der Merwe et al. |

FOREIGN PATENT DOCUMENTS

| | | |
|---|---|---|
| CA | 1027501 A1 | 3/1978 |
| CA | 1055868 | 6/1979 |
| CA | 1059052 A1 | 7/1979 |
| CA | 1072474 A1 | 2/1980 |
| CA | 1081641 A1 | 7/1980 |
| CA | 1111782 A1 | 11/1981 |
| CA | 1165712 A1 | 4/1984 |
| CA | 1237689 A1 | 6/1988 |
| CA | 1245990 A1 | 12/1988 |
| CA | 1247550 | 12/1988 |
| CA | 1249414 A1 | 1/1989 |
| CA | 1263331 A1 | 11/1989 |
| CA | 1267860 A1 | 4/1990 |
| CA | 1272975 A1 | 8/1990 |
| CA | 2012305 A1 | 9/1990 |
| CA | 2029795 A1 | 5/1991 |
| CA | 1291957 C | 11/1991 |
| CA | 1293465 C | 12/1991 |
| CA | 2021185 A1 | 1/1992 |
| CA | 2053016 A1 | 5/1992 |
| CA | 2053086 A1 | 4/1993 |
| CA | 2055213 A1 | 5/1993 |
| CA | 2075108 A1 | 1/1994 |
| CA | 2098656 A1 | 12/1994 |
| CA | 2123076 A1 | 11/1995 |
| CA | 2165865 A1 | 6/1997 |
| CA | 2174801 | 10/1997 |
| CA | 2188264 A1 | 4/1998 |
| CA | 2191517 A1 | 5/1998 |
| CA | 2200899 A1 | 9/1998 |
| CA | 2232929 A1 | 9/1998 |
| CA | 2149737 C | 3/1999 |
| CA | 2217300 A1 | 3/1999 |
| CA | 2254048 A1 | 5/1999 |
| CA | 2195604 C | 11/1999 |
| CA | 2350907 A1 | 5/2000 |
| CA | 2272045 A1 | 11/2000 |
| CA | 2304972 A1 | 10/2001 |
| CA | 2350001 A1 | 12/2002 |
| CA | 2353109 A1 | 1/2003 |
| CA | 2387257 A1 | 11/2003 |
| CA | 2527058 A1 | 3/2004 |
| CA | 2425840 A1 | 10/2004 |
| CA | 2454942 A1 | 7/2005 |
| CA | 2455011 A1 | 7/2005 |
| CA | 2726122 A1 | 7/2005 |
| CA | 2750837 A1 | 7/2005 |
| CA | 2750845 A1 | 7/2005 |
| CA | 2750934 A1 | 7/2005 |
| CA | 2750936 A1 | 7/2005 |
| CA | 2750939 A1 | 7/2005 |
| CA | 2750995 A1 | 7/2005 |
| CA | 2751587 A1 | 7/2005 |
| CA | 2751773 A1 | 7/2005 |
| CA | 2799354 A1 | 7/2005 |
| CA | 2799400 A1 | 7/2005 |
| CA | 2799739 A1 | 7/2005 |
| CA | 2520943 A1 | 4/2006 |
| CA | 2490734 A1 | 6/2006 |
| CA | 2502329 A1 | 9/2006 |
| CA | 2521248 A1 | 3/2007 |
| CA | 2524110 A1 | 4/2007 |
| CA | 2526336 A1 | 5/2007 |
| CA | 2567185 A1 | 4/2008 |
| CA | 2610122 A1 | 5/2008 |
| CA | 2610124 A1 | 5/2008 |
| CA | 2573633 A1 | 7/2008 |
| CA | 2673961 A1 | 7/2008 |

(56) References Cited

FOREIGN PATENT DOCUMENTS

| | | | |
|---|---|---|---|
| CA | 2582059 A1 | 9/2008 |
| CA | 2588043 A1 | 11/2008 |
| CA | 2606312 A1 | 4/2009 |
| CA | 2610052 A1 | 5/2009 |
| CA | 2616036 A1 | 6/2009 |
| CA | 2654611 A1 | 8/2009 |
| CA | 2630392 A1 | 11/2009 |
| CA | 2669059 A1 | 12/2009 |
| CA | 2638120 A1 | 1/2010 |
| CA | 2673981 A1 | 1/2010 |
| CA | 2673982 A1 | 1/2010 |
| CA | 2641294 A1 | 4/2010 |
| CA | 2655852 A1 | 4/2010 |
| CA | 2683374 A1 | 4/2010 |
| CA | 2643893 A1 | 5/2010 |
| CA | 2647855 A1 | 7/2010 |
| CA | 2649928 A1 | 7/2010 |
| CA | 2652355 A1 | 8/2010 |
| CA | 2653032 A1 | 8/2010 |
| CA | 2653058 A1 | 8/2010 |
| CA | 2689684 A1 | 8/2010 |
| CA | 2657360 A1 | 9/2010 |
| CA | 2657801 A1 | 10/2010 |
| CA | 2661579 A1 | 10/2010 |
| CA | 2711136 A1 | 10/2010 |
| CA | 2666025 A1 | 11/2010 |
| CA | 2708416 A1 | 12/2010 |
| CA | 2674246 A1 | 1/2011 |
| CA | 2708048 A1 | 1/2011 |
| CA | 2678818 A1 | 3/2011 |
| CA | 2701317 A1 | 3/2011 |
| CA | 2717406 A1 | 4/2011 |
| CA | 2729457 A1 | 7/2011 |
| CA | 2733862 A1 | 7/2011 |
| CA | 2705055 A1 | 11/2011 |
| CA | 2768852 A1 | 11/2011 |
| CA | 2748477 A1 | 3/2012 |
| CA | 2752558 A1 | 3/2012 |
| CA | 2730467 A1 | 8/2012 |
| CA | 2735311 A1 | 9/2012 |
| CA | 2737410 A | 10/2012 |
| CA | 2740935 A | 11/2012 |
| CN | 1187300 A | 7/1998 |
| EP | 0059106 A2 | 9/1982 |
| GB | 587798 A | 5/1947 |
| GB | 2044796 A | 10/1980 |
| GB | 2145730 A | 4/1985 |
| JP | S56150407 A | 11/1981 |
| JP | S57200402 A | 12/1982 |
| JP | S6285415 U | 5/1987 |
| RU | 2065455 C1 | 8/1996 |
| RU | 2078095 C1 | 4/1997 |
| RU | 2096438 C1 | 11/1997 |
| WO | 2007102819 A1 | 9/2007 |
| WO | 2009111871 A1 | 9/2009 |
| WO | 2010088388 A1 | 8/2010 |

OTHER PUBLICATIONS

Dispersion Technology, Inc., "Model DT-1201 . . . Acoustic and electro-acoustic spectrometer", Particle size and zeta potential measurement.
Csiro Minerals, UltraPS—Ultrasonic Particle Size Analyser, www.minerals.csiro.au.
Wedd, "Determination of Particle Size Distributions Using Laser Diffraction", Educ.Reso. for Part. Techn. 032Q-Wedd, pp. 1-4.
Rahmani et al., "Settling Properties of of Asphaltene Aggregates", Abstract, Energy Fuels, 2005, 19 (3), pp. 1099-1108.
Rahmani et al., "Fractal structure of asphaltene aggregates", Abstract, Journal of Colloid and Interface Science, vol. 285, Issue 2, May 15, 2005, pp. 599-608.
A John Brooks Website, Spraying pumping filtering, Automated Retractable Nozzle System, FluidHandlingSolutions.com.
Liang et al., "Experimental and Analytical Study of Direct Contact Condensation of Steam in Water" Nucl. Eng. Des., 147, Issue 3, Apr. 1994, pp. 425-435.
Peramanu et al., "Flow loop apparatus to study the effect of solvent, temperature and additives on asphaltene precipitation" Journal of Petroleum Science and Engineering, vol. 23, Issue 2, Aug. 1999, pp. 133-143.
Andrews et al. "Great Canadian Oil Sands Experience in Commercial Processing of Athabasca Tar Sands" American Chemical Society San Francisco Meeting Apr. 2-5, 1968, p. F5-F18.
Mitchell et al. "The solubility of asphaltenes in hydrocarbon solvents" Fuel, 1973, N. 02, vol. 52, p. 149-152.
Kemp, "Pinch Analysis and Process Integration, A User Guide on Process Integration for the Efficient Use of Energy", Second edition, Elsevier 2007.
Svreck et al "Successfully Specify Three-Phase Separators" Chemical Engineering Progress, Sep. 1994, p. 29-40.
Svreck et al. "Design Two-Phase Separators within the Right Limits" Chemical Engineering Progress, Oct. 1993, p. 53-60.
Fu et al."New technique for determination of diffusivities of volatile hydrocarbons in semi-solid bitumen", Fuel, 1979, vol. 58, August, pp. 557-560.
Kamoun et al."High Speed Shadowgraphy Investigations of Superheated Liquid Jet Atomization", ILASS—Americas 22nd Annual Conference on Liquid Atomization and Spray Systems, Cincinnati Ohio, May 2010.
Duan et al.'s "Numerical Analyses of Flashing Jet Structure and Droplet Size Characteristics" Journal of Nuclear Science and Technology, 2006, vol. 43, No. 3, p. 285-294.
Sou et al., "Effects of Cavitation in a Nozzle on liquid Jet atomization" International Journal of Heat and Mass Transfer; vol. 50, p. 3575-3582, 2007.
Ransom et al., "The relaps choke flow model and application to a large scale flow test", The American Society of Mechanical Engineers, Heat Transfer Division, 1980, Saratoga, New York.
Power,"Froth Treatment: Past, Present &Future" Oil Sand Symposium, University of Alberta, May 3-5, 2004.
Rahmani, "Shear-Induced Growth of Asphaltene Aggregates" Oil Sand Symposium, University of Alberta, May 4, 2004.
Paul et al. "Handbook of Industrial Mixing: Science and Practice" Wiley Interscience 2004, p. 391-477.
Blevins "Applied fluid dynamics handbook", Van Nostrand Reinhold Company 1984, p. 80-83.
Wu et al., "Experimental study on steam plume and temperature distribution for sonic jet" J. Phys.: Conf.Ser. 147 2009, 012079.
Yeon et al., "An Experimental Investigation of Direct Condensation of Steam Jet in Subcooled Water" Journal of Korean Nuclear Society vol. 29, No. 1, pp. 45-57, Feb. 1997.
Long et al., "Structure of water/solids/asphaltenes aggregates and effect of mixing temperature on settling rate in solvent-diluted bitumen" Fuel 2004, vol. 83, p. 823-832.
Rahimi et al., "Partial Upgrading of Athabasca Bitumen Froth by Asphaltene Removal", Unitar International Conference on Heavy Crude and Tar Sande, No. 1998.074, p. 1-8.
Hoehenberger, "Water Treatment, Cycle Chemistry, Boiler Operation and Related Problems/Failures on Steam Generator Systems > 30 bar", TÜV SÜD Industry Services, 2006, p. 1-14.
Schroyer, "Understand the Basics of Steam Injection Heating", Chemical Engineering Progress, Hydro-Thermal Corporation, May 1997, p. 1-4.
Prosonix, "PSX Steam Jet Diffuser . . . Technology That Makes a Difference", PSX Jet Diffuser Feb. 9, 2011.
Prosonix, "ProSonix Technical Bulletin", TB-4 Liquid & Steam Pressure Relationship.
Prosonix, "PSX Technical Bulletin", TB-7 Internally Modulated Steam Control 0210.
Prosonix, "Sparging Efficiency vs. Direct Steam Injection", TB-6 Sparging Efficiency & Performance Dec. 10, 2010.
Siemens, "Pictures of the Future", Spring 2006, Power Plants—Siemens Global Website, http://www.siemens.com/innovation/en/publikationen/publications_pof/pof_spring_2006/infrastructures_articles/power_plants.htm.
George, "Mining for Oil", Scientific American, Mar. 1998, p. 84-85.

(56) References Cited

OTHER PUBLICATIONS

Speight, "Deasphalting and Dewaxing Processes", The Chemistry and Technology of Petroleum, Fourth Edition, Chapter 19, CRC Press 2006.
Jeribi et al., "Adsorption Kinetics of Asphaltenes at Liquid Interfaces", Journal of Colloid and Interface Science, vol. 256, Issue 2, Dec. 15, 2002, pp. 268-272.
Branan, "Pocket Guide to Chemical Engineering" Elsevier Science & Technology Books, Nov. 1999.
Perry, "Perry's Chemical Engineers' Handbook" (7th Ed.), 1997.
Clarke et al., "Asphaltenes precipitation from Cold Lake and Athabasca bitumens", Petroleum Science and Technology, 1998, 16:3-4, p. 287-305.
Al-Atar, "Effect of Oil Compatibility and Resins/Asphaltenes Ratio on Heat Exchanger Fouling of Mixtures Containing Heavy Oil", Master Degree Thesis report, The University of British Columbia, Feb. 2000.
Gearhart, "ROSE® process offers energy savings for solvent extraction", Proceedings from the Fifth Industrial Energy Technology Conference vol. II, Houston, TX, Apr. 17-20, 1983, p. 823-835.
Clarke et al., "Asphaltene precipitation: detection using heat transfer analysis, and inhibition using chemical additives" Fuel, vol. 76, Issue 7, May 1997, p. 607-614.
Shell Canada Limited, Application for Approval of the Jackpine Mine—Phase 1, ERCB application No. 1271285, May 2002.
Imperial Oil Ressources Ventures Limited, Application for the Imperial Oil Resources Ventures Limited (Imperial Oil) and ExxonMobil Canada Properties (ExxonMobil Canada) Kearl Oil Sands Project—Mine Development (Kearl Project), ERCB Application No. 1408771, Jul. 12, 2005.
Shell Canada Limited, Application for the Approval of Muskeg River Mine Project, ERCB Application No. 970588, Dec. 19, 1997.
Beckman Coulter, Particle Size and Size Distribution Analysis, Coulter Counter.com, pp. 1-3.
Outokumpu Technology, Slurry particle size analyzer, PSI 200 TM, 2006, pp. 1-8.
Johnson, Particle size distribution in clays, Clays and Clay Minerals, pp. 89-91.
Buckley et al., Solubility of the Least-Soluble Asphaltenes, Asphaltenes, Heavy Oils, and Petroleomics, Springer, 2007, Chapter 16, pp. 401-437.
Gerson et al., The Relation of Surfactant Properties to the Extraction of Bitumen from Athabasca Tar Sand by a Solvent-Aqueous-Surfactant Process, Chemistry for Energy, American Chemical Society, 1979, Chapter 6, pp. 66-79.
Nour et al., Characterization and Demulsification of Water-in-crude Oil Emulsions, Journal of Applied Sciences, vol. 7, issue 10, 2007, pp. 1437-1441.
Malcolmson et al., In-Line Particle Size Measurements for Cement and Other Abrasive Process Environments, For Presentation at the IEEE/PCA 40th Cement Industry Technical Conference, 1998, pp. 1-13.
International Search Report in corresponding PCT/CA2012/050108 mailed Jun. 8, 2012.
Written Opinion in corresponding PCT/CA2012/050108 mailed Jun. 8, 2012.
William L. Luyben, "Heat-Exchanger Bypass Control", Ind. Eng. Chem. Res. 2011, 50, 965-973.
Dutta-B, "Principles of Mass Transfer and Separation Processes", p. 344, 2009.
Schaschke, Carl. (2014). Dictionary of Chemical Engineering. Oxford University Press. p. 67. Online version available at:http://app.knovel.com/hotlink/toc/id:kpDCE00021/dictionary-chemical-engineering/dictionary-chemical-engineering.
Imran Ali, "Process Heating by Direct Steam Injection", Pharmaceutical Guide; Dec. 2010.
Choung, J. et al., "Effect of Temperature on the Stability of Froth Formed in the Recycle Process Water of Oil Sands Extraction", The Canadian Journal of Chemical Engineering, vol. 82, Aug. 2004, pp. 801-806.
Wiwchar, K. et al., "Column flotation in an oilsand application", Proceedings 36th Annual Meeting of the Canadian Mineral Processors, Ottawa, Ontario, Canada, Jan. 20-22, 2004.
Cleyle, P. et al., "Column Flotation Testing at Suncor Energy Inc.", Oilsand 2006 Conference, CD, University of Alberta, Feb. 22-24, 2006.
Finch, J. et al. "Column Flotation", 1st ed. Pergamon Press, 1990, pp. 1-7, 75-79, 82-89, 148-149, 152-159.
Baczek, "Paste Thickening Design Evolving to Higher Capacities and Efficiencies", International Minimizing Supplement to Paste Tailing Management, Mar. 2007. 16 pages.
Versteeg et al., "An Introduction to Computational Fluid Dynamics: the Finite Volume Method", 2nd Edition, Pearson Prentice Hall, First published 1995 and 2nd Edition published 2007, pp. 9, 33-77, 88-97, 78-87, 98-114, 115, 131-133, 156-164, 186-196, 256-264.
Ferziger et al., "Computational Methods for Fluid Dynamics", 3rd Edition, Springer, 2002, pp, 142-151, 188-206, 226-245, 265-307, 324-328.
Hobbs, D.M., "Optimization of a static mixer using dynamical systems techniques", published 1998, Elsevier Science, Chemical Engineering, vol. 53, No. 18, pp. 3199-3213.
Godard, et al., "A Review of Suncor Energy's Millennium Extraction Process", Proceedings 36th Annual Meeting of the Canadian Mineral Processors, pp. 141-152 (2004).
Mankowski et al., "Syncrude's Low Energy Extraction Process: Commercial Implementation", Proceedings 31st Annual Meeting of the Canadian Mineral Processors, pp. 154-181 (1999).
"Choked Flow of Gases", O'Keefe Controls Co., pp. 38, 16-18 (2000).

PROCESS AND UNIT FOR SOLVENT RECOVERY FROM SOLVENT DILUTED TAILINGS DERIVED FROM BITUMEN FROTH TREATMENT

FIELD OF THE INVENTION

The present invention relates to the recovery of solvent from solvent diluted tailings derived from a bitumen froth treatment operation.

BACKGROUND

In bitumen froth treatment processes, solvent or diluent is added to a bitumen froth to separate a diluted bitumen stream for further processing. In a paraffinic bitumen froth treatment process, for example, bitumen froth derived from oil sands is combined with paraffinic solvent and then supplied to a settling vessel in which a bitumen rich fraction is separated from a bottoms fraction rich in asphaltenes, water, solvent and solids as well as residual amounts of bitumen. This bottoms fraction is often referred to as solvent diluted tailings or froth treatment tailings.

Solvent diluted tailings are preferably treated to recuperate the paraffinic solvent, which is subject to environmental discharge regulations and a valuable commodity, prior to disposal of the resulting solvent recovered tailings containing primarily water and solids. Solvent diluted tailings may be treated in tailings solvent recovery units that include flash vessels.

Flash vessels conventionally used to recover diluent from froth treatment tailings are specified for a feed flow and feed temperature so that, at the stage column pressure with optional stripping, steam vaporizes the diluent for recovery in the overhead condensing system.

However, variations in feed flow and feed temperature result in several challenges that affect recovery and unit reliability. High feed flows can increase liquid loading on flash column internals which directionally increases the time required for diluent to separate. In addition, low feed flows can cause "short circuiting" in the flash column when feed does not adequately cover internals and tends to promote depositions of froth treatment tailings minerals, bitumen and asphaltenes on the surfaces of internals. Furthermore, high feed temperatures can increase the column pressure when water that flashes with diluent exceeds the condensing capacity of the overhead system. Also, high velocities in the column can encourage unwanted entrainment of particulates that foul the overhead system. Low feed temperatures may also reduce the flashing of diluent from froth treatment tailings. These problems and challenges may owe to a number of factors, including feed properties of the bitumen froth, operating conditions of the froth treatment settling vessels and other parameters of the froth treatment plant.

A conventional approach currently practiced includes the addition of water to froth treatment tailings to ensure minimum line velocities are maintained to suspend solids in froth treatment tailings and avoid line plugging. This water may comprise waste water from various sources without control on temperature. Variations in froth treatment tailings both from flow and temperature perspectives have been observed. However, the implications of adding water on performance of flash separation may include several drawbacks.

As more general background on paraffinic froth treatment (PFT), for which solvent diluted tailings are derived, extraction processes are used to liberate and separate bitumen from oil sand so the bitumen can be further processed. Numerous oil sand extraction processes have been developed and commercialized using water as a processing medium. One such water extraction process is the Clarke hot water extraction process, which recovers the bitumen product in the form of a bitumen froth stream. The bitumen froth stream produced by the Clarke hot water process contains water in the range of 20 to 45%, more typically 30% by weight and minerals from 5 to 25%, more typically 10% by weight which must be reduced to levels acceptable for downstream processes. At Clarke hot water process temperatures ranging from 40 to 80° C., bitumen in bitumen froth is both viscous and has a density similar to water. To permit separation by gravitational separation processes, commercial froth treatment processes involve the addition of a diluent to facilitate the separation of the diluted hydrocarbon phase from the water and minerals. Initial commercial froth treatment processes utilized a hydrocarbon diluent in the boiling range of 76-230° C. commonly referred to as a naphtha diluent in a two stage centrifuging separation process. Limited unit capacity, capital and operational costs associated with centrifuges promoted applying alternate separation equipment for processing diluted bitumen froth. In these processes, the diluent naphtha was blended with the bitumen froth at a weight ratio of diluent to bitumen (D/B) in the range of 0.3 to 1.0 and produced a diluted bitumen product with typically less than 4 weight percent water and 1 weight percent mineral which was suitable for dedicated bitumen upgrading processes. Generally, operating temperatures for these processes were specified such that diluted froth separation vessels were low pressure vessels with pressure ratings less than 105 kPag. Other froth separation processes using naphtha diluent involve operating temperatures that require froth separation vessels rated for pressures up to 5000 kPag. Using conventional vessel sizing methods, the cost of pressure vessels and associated systems designed for and operated at this high pressure limits the commercial viability of these processes.

Heavy oils such as bitumen are sometimes described in terms of relative solubility as comprising a pentane soluble fraction which, except for higher molecular weight and boiling point, resembles a distillate oil; a less soluble resin fraction; and a paraffinic insoluble asphaltene fraction characterized as high molecular weight organic compounds with sulphur, nitrogen, oxygen and metals that are often poisonous to catalysts used in heavy oil upgrading processes. Paraffinic hydrocarbons can precipitate asphaltenes from heavy oils to produce deasphalted heavy oil with contaminate levels acceptable for subsequent downstream upgrading processes. Contaminants tend to follow the asphaltenes when the asphaltenes are precipitated by paraffinic solvents having compositions from $C_3$ to $C_{10}$ when the heavy oil is diluted with 1 to 10 times the volume of solvent.

High water and mineral content distinguish bitumen froth from the heavy oil deasphalted in the above processes. Some early attempts to adapt deasphalting operations to processing bitumen from oil sands effected precipitation of essentially a mineral free, deasphalted product, the ability to vary the amount of asphaltene precipitated, and the enhancement of asphaltene precipitation by addition of water and chemical agents.

Recent investigations and developed techniques in treating bitumen froth with paraffinic use froth settling vessels (FSV) arranged in a counter-current flow configuration. In process configurations, counter-current flow refers to a processing scheme where a process medium is added to a stage in the process to extract a component in the feed to that stage, and the medium with the extracted component is blended into the feed of the preceding stage. Counter-current flow configurations are widely applied in process operations to achieve both product quality specifications and optimal recovery of a component with the number of stages dependent on the interaction between the desired component in the feed stream and the selected medium, and the efficiency of stage separations. In deasphalting operations processing heavy oil with low mineral solids, separation using counter-current flow can be achieved within a single separation vessel. However, rapidly setting mineral particles in bitumen froth preclude using a single separation vessel as this material tends to foul the internals of conventional deasphalting vessels.

A two stage paraffinic froth treatment process is disclosed in Canadian Patent No. 2,454,942. In a froth separation plant, bitumen froth is mixed with overflow product from the second stage settler such that the solvent to bitumen ratio in the diluted froth stream is above the threshold to precipitate asphaltenes from the bitumen froth. For paraffinic froth treatment processes with pentane as the paraffinic solvent, the threshold solvent to bitumen ratio as known in the art is about 1.2 which significantly increases the feed volume to the settler. The first stage settler separates the diluted froth into a high dilute bitumen stream comprising a partially to fully deasphalted diluted bitumen with a low water and mineral content, and an underflow stream containing the rejected asphaltenes, water, and minerals together with residual maltenes from the bitumen feed and solvent due to the stage efficiency. The first stage underflow stream is mixed with hot recycled solvent to form a diluted feed for the second stage settler. The second stage settler recovers residual maltenes and solvent to the overflow stream returned to the first stage vessel and froth separation tailings. It is important to recognize the different process functions of stages in a counter-current process configuration. In this case, the operation of first stage settler focuses on product quality and the second stage settler focuses on recovery of residual hydrocarbon from the underflow of the first stage settler.

The process may be operated at temperatures that require controlling the pressure in either settler stage to limit solvent vaporization. The concentration of solvent in diluted bitumen and temperature for a specific paraffinic solvent such as pentane determine the solubility and hence the rejection of asphaltenes. While low asphaltene rejection maximizes bitumen recovery, the asphaltene content may limit processing options in upgrading operations particularity those based on hydrogen addition.

Furthermore, froth treatment tailings from either naphthenic or paraffinic froth treatment process contain diluent associated with unrecovered bitumen and the cost and environmental impact preclude directly discharging froth treatment tailings to tailings ponds.

Various treatment and recovery schemes are disclosed in literature. In one process, froth treatment tailings from the froth treatment plant are introduced to a flash vessel with internal shed decks maintained at sub-atmospheric pressures. Steam is introduced below the internals and the major portion of the diluent vaporizes together with water. The flashed vapours are removed and cooled to condense diluent and water which separate by gravity settling. Non-condensed vent gases are withdrawn from the condenser to maintain the sub-atmospheric pressure. The flashed tailings are pumped from the flash vessel to tailings disposal.

While diluent recovery for this process, which is disclosed in Canadian Patent No. 1,027,501 (Simmer), has been identified at 86%, actual practise as disclosed in Canadian Patent No. 2,272,045 (Brown et al.) achieve recoveries of only 60 to 65% of the diluent. This lower recover has been attributed to flashing at the feed inlet inducing feed to bypass the shed decks negating addition of steam below the shed decks. A proposed solution identified by Brown et al. was to operate the flash vessel at near atmospheric pressure which permitted feed distribution over the shed decks and increasing the steam addition to maintain vessel temperature to about 100° C. which could increase naphtha diluent recovery to 80% and the process could be applied to paraffinic diluent operations.

Recent investigations into attaining diluent recoveries as disclosed in Brown et al. identified variations in froth treatment operations, processing froth treatment slops, addition of process water for flushing equipment and maintenance of minimum velocities in slurry lines, which result in feed to the tailings treatment flash column varying by about +/−25% with respect to flow and about +/−10% with respect to temperature. The variation in feed flows and temperatures translates to varying the enthalpy of the feed stream to the column.

The diluent recovery process disclosed by Simmer flashes feed to a flash temperature such that the enthalpy of vaporized flash components matches enthalpy released from the flash liquid and the flash temperature governs vapour pressures of vaporizing components. Given the relative volatility of diluent hydrocarbons, one can expect a direct relation between feed temperature, flash temperature and diluent recovery. However, the investigation identified that increased feed temperatures for the same feed flow did not proportionately translate to increased diluent recovery due to increased vaporization of water. Stable operation of the column in terms of flash temperature and pressure was found marginally below the boiling point of water for the operating pressure and with small increases in feed enthalpy resulting in upsets as the water can essentially boil.

The upsets affect the flash column in various ways, two of which are the following. Firstly, boiling on shed decks results in equipment damage to the extent that the shed decks experience frequent structural failure. Secondly, the vapour velocity in the column increases, for instance by an order of magnitude, exceeding design guidelines such a set out in "*Design Two-Phase Separators within the Right Limits*" W. Svrcek, et al. Chemical Engineering Progress, October 1993, which leads to problems related to entraining solids and bitumen into the overhead system.

In the overhead system, bitumen acts a binder for the solids to adhere on surfaces in the overhead system. The adherence of solids to components of the overhead system restricts vapour flow to the separator. The adherence of solids on condenser heat transfer surfaces reduces cooling and condensing of vapours which increases the non-condensed gases to be vented. Directionally, solids adhering on surfaces in the overhead system increases column pressure which reduces feed flashing and actual diluent recoveries, for instance to 60 to 65% over the operational cycle. The contribution of increased steam of Brown et al. to improve diluent recoveries due to the reduced partial pressure created by the superheated steam is largely offset by the increased water vapour reporting to an overhead system restricted by the adherence of solids. Solids adherence to surfaces increases the pressure drop between flash vessel and condensate drum; this, in turn, increases the flash pressure, which lowers the extent to which diluent flashes at higher pressure. Over the operating cycle, the deposits of solids cause column performance to deteriorate and regaining performance is achieved by shutting down the column and associated systems for repair and cleaning.

It is clear that the known techniques and methods of treating froth treatment tailings have several drawbacks and shortcomings.

SUMMARY OF THE INVENTION

The present invention responds to the above-mentioned need by providing a process and unit for tailings solvent recovery in connection with a froth treatment operation.

In one embodiment, there is provided a tailings solvent recovery unit (TSRU) for recovering a solvent from a solvent diluted tailings derived from a bitumen froth treatment process, the TSRU comprising a separation apparatus for receiving the solvent diluted tailings and producing a solvent component and a solvent recovered tailings component, the separation apparatus comprising a vessel comprising a solvent removal section for accommodation removal of the solvent from the solvent diluted tailings and a bottom section for accumulation of the solvent recovered tailings component; a tailings outlet for releasing the solvent recovered tailings component from the vessel; a solvent outlet for releasing the solvent component from the vessel as a vaporized solvent; a tailings inlet for supplying a variable flow of the solvent diluted tailings to the vessel; a tailings recycle line in fluid connection with the tailings inlet for recycling a portion of the solvent recovered tailings component as a recycled tailings component into the variable flow of the solvent diluted tailings to produce a flow rate controlled feed for introduction into the vessel.

In one optional aspect, the separation apparatus is a stripping apparatus, the vessel is a stripping vessel and the solvent removal section is a stripping section, the separation apparatus comprising a stripping fluid inlet for providing a stripping fluid to the stripping vessel to facilitate separation of the solvent component from the solvent recovered tailings component.

In one optional aspect, the TSRU also has a feed heat exchanger associated with the tailings inlet for heating the flow rate controlled feed to a controlled inlet temperature.

In one optional aspect, the feed heat exchanger is configured to heat the flow rate controlled feed sufficiently to promote a constant feed temperature into the stripping vessel.

In one optional aspect, the TSRU also has a recycle heat exchanger associated with the tailings recycle line for heating the recycled tailings component prior to introduction into the solvent diluted tailings.

In one optional aspect, the recycle heat exchanger is configured to heat the recycled tailings component sufficiently to promote a constant feed temperature into the stripping vessel.

In one optional aspect, the TSRU also has a condenser for receiving and condensing the vaporized solvent to produce a condensed solvent.

In one optional aspect, the TSRU also has a separator for receiving the condensed solvent and producing vapour, purified recovered solvent and produced water.

In one optional aspect, the TSRU also has at least one water recycle line for recycling at least a portion of the produced water back into the stripping vessel.

In one optional aspect, the at least one water recycle line is fluidly connected to the stripping vessel below a liquid level of a pool of the solvent recovered tailings component in the stripping vessel.

In one optional aspect, the tailings recycle line is configured and sized such that the ratio of the recycled tailings component to the solvent recovered tailings component is between about 50% and about 200% in standard operating mode.

In one optional aspect, the tailings recycle line is configured and sized such that the ratio of the recycled tailings component to the solvent recovered tailings component is between about 80% and about 120% in standby operating mode.

In one optional aspect, the stripping vessel is a first stripping vessel and the stripping apparatus further comprises a second stripping vessel arranged in series with the first stripping vessel, the first stripping vessel producing a first solvent recovered tailings component comprising residual solvent, the second stripping vessel receiving the first solvent recovered tailings and producing a second solvent recovered tailings component and a second vaporized solvent.

In another optional aspect, the TSRU includes a second tailings heat exchanger for heating the first solvent recovered tailings component prior to introduction into the second stripping vessel.

In one optional aspect, the second stripping vessel comprises a second tailings recycle line for recycling a portion of the second solvent recovered tailings as a second recycled tailings component into the first solvent recovered tailings to produce a flow rate controlled second feed for introduction into the second stripping vessel.

In another optional aspect, the TSRU includes a second feed heat exchanger for heating the flow rate controlled second feed to a controlled inlet temperature.

In one optional aspect, the second feed heat exchanger is configured to heat the flow rate controlled second feed sufficiently to promote a constant second feed temperature into the second stripping vessel.

In another optional aspect, the TSRU includes a second recycle heat exchanger for heating the second recycled tailings component prior to introduction into the first solvent recovered tailings.

In another optional aspect, the TSRU includes a second separator for separating the second condensed solvent into a separated solvent component containing residual water and a vapour component.

In one optional aspect, the second separator is a knock-out drum.

In another optional aspect, the TSRU includes a vapour recycle line for recycling the vapour component back into the paraffinic solvent component released from the first stripping vessel.

In one optional aspect, the vapour recycle line is associated with a vacuum package.

In another optional aspect, the TSRU includes a separated solvent recycle line for recycling at least a portion of the separated solvent component back into the first separator.

In one optional aspect, the separated solvent recycle line is configured to recycle all of the separated solvent component back into the first separator.

In one optional aspect, the solvent is a paraffin derived from a paraffinic bitumen froth treatment process.

In one optional aspect, the solvent is naphtha derived from a naphthenic bitumen froth treatment process.

The invention also provides a tailings solvent recovery process for recovering a solvent from a variable flow of a solvent diluted tailings derived from a bitumen froth treatment operation, the process comprising separating the solvent diluted tailings to produce a recovered solvent component and a solvent recovered tailings component; discharging the solvent recovered tailings component as a discharged solvent recovered tailings component; and recycling a portion of the solvent recovered tailings component as a recycled tailings component back into the variable flow of the solvent diluted tailings to produce a flow rate controlled feed for the separating.

In one optional aspect, the separating of the solvent diluted tailings comprises stripping.

In another optional aspect, the process includes feed heating the flow rate controlled feed to a controlled inlet temperature for the separating.

In one optional aspect, the feed heating is performed to promote a constant feed temperature for the separating.

In another optional aspect, the process includes recycle heating the recycled tailings component prior to introduction into the solvent diluted tailings.

In one optional aspect, the recycle heating is performed to promote a constant feed temperature for the separating.

In yet another optional aspect, the process includes condensing the vaporized solvent to produce a condensed solvent.

In another optional aspect, the process includes separating the condensed solvent into vapour, purified recovered solvent and produced water.

In another optional aspect, the process includes recycling at least a portion of the produced water back into the separating of the solvent diluted tailings.

In one optional aspect, the recycling of the produced water is performed below a liquid level of a pool of the solvent recovered tailings component.

In one optional aspect, recycling of the recycled tailings component is performed at a ratio of the recycled tailings component to the solvent recovered tailings component of between about 50% and about 200% in standard operating mode.

In one optional aspect, recycling of the recycled tailings component is performed at a ratio of the recycled tailings component to the solvent recovered tailings component of between about 80% and about 120% in standby operating mode.

In one optional aspect, the separating comprises stripping which comprises a first stripping stage and a second stripping stage arranged in series, the first stripping stage producing a first solvent recovered tailings component comprising residual solvent, the second stripping stage receiving the first solvent recovered tailings and producing a second solvent recovered tailings component and a second vaporized solvent.

In another optional aspect, the process includes heating the first solvent recovered tailings component prior to introduction into the second stripping stage.

In another optional aspect, the process includes recycling a portion of the second solvent recovered tailings as a second recycled tailings component into the first solvent recovered tailings to produce a flow rate controlled second feed for introduction into the second stripping stage.

In another optional aspect, the process includes heating the flow rate controlled second feed to a controlled inlet temperature for the second stripping stage.

In one optional aspect, the heating of the flow rate controlled second feed is performed to promote a constant second feed temperature into the second stripping stage.

In another optional aspect, the process includes heating the second recycled tailings component prior to introduction into the first solvent recovered tailings.

In another optional aspect, the process includes separating the second condensed solvent into a separated solvent component containing residual water and a vapour component.

In one optional aspect, the separating of the he second condensed solvent is performed in a knock-out drum.

In another optional aspect, the process includes recycling the vapour component back into the paraffinic solvent component released from the first stripping stage.

In one optional aspect, the recycling of the vapour component is aided by a vacuum package.

In another optional aspect, the process includes recycling at least a portion of the separated solvent component back for separation with the condensed solvent.

In another optional aspect, the process includes recycling all of the separated solvent component back for separation with the condensed solvent.

In one optional aspect, the solvent is a paraffin derived from a paraffinic bitumen froth treatment process.

In one optional aspect, the solvent is naphtha derived from a naphthenic bitumen froth treatment process.

The invention also provides a method of controlling feed flow rate to a tailings solvent recovery vessel for recovering a solvent from a solvent diluted tailings derived from a bitumen froth treatment process, the method comprising recycling an amount of underflow tailings from the tailings solvent recovery vessel back into the solvent diluted tailings to produce a flow rate controlled tailings feed and to allow sufficient pressure on the flow rate controlled tailings feed to avoid vapour flashing prior to the tailings solvent recovery vessel; and introducing the flow rate controlled tailings feed into the tailings solvent recovery vessel.

In one optional aspect, the method includes moderating the temperature of the flow rate controlled tailings feed to produce a flow rate and temperature controlled tailings feed.

In another optional aspect, the tailings solvent recovery vessel comprises a stripping column.

In another optional aspect, the tailings solvent recovery vessel comprises a plurality of stripping columns arranged in series.

In another optional aspect, the method includes applying the pressure on the flow rate controlled tailings feed via a valve device.

In another optional aspect, the method includes applying the pressure on the flow rate controlled tailings feed via a flow restriction.

In another optional aspect, the method includes preheating the amount of the underflow tailings stream prior to introduction into the solvent diluted tailings.

In another optional aspect, the method includes preheating the flow rate controlled tailings feed using a heat exchanger.

In another optional aspect, the method includes releasing solvent vapour from the tailings solvent recovery vessel; recovering produced water from the solvent vapour; and returning the produced water back into the tailings solvent recovery vessel.

In another optional aspect, the produced water is returned into a pool of accumulated solvent recovered tailings in the tailings solvent recovery vessel.

In another optional aspect, the solvent is a paraffinic solvent and the solvent diluted tailings are derived from a paraffinic bitumen froth treatment process.

In another optional aspect, the tailings solvent recovery vessel comprises a first stage column fed at a temperature of between about 70° C. and about 90° C.

In another optional aspect, the first stage column is fed at a temperature above a highest froth treatment process temperature.

In another optional aspect, the tailings solvent recovery vessel comprises a second stage column operated between about 20 kPaa and about 100 kPaa.

In another optional aspect, the paraffin comprises preferentially retained paraffins that are preferentially retained within asphaltene-bitumen matrices with respect other paraffins of the solvent due to lower diffusivity, and the process comprises providing a residence time of the solvent diluted tailings in the solvent recovery vessel to promote recovery of the preferentially retained paraffins.

In another optional aspect, the preferentially retained paraffins comprise iso-paraffins.

In another optional aspect, the solvent is naphtha and the solvent diluted tailings are derived from a naphthenic bitumen froth treatment process.

In another optional aspect, the method includes operating the solvent recovery vessel at a temperature between about 65° C. and about 85° C.

In another optional aspect, the method includes operating the solvent recovery vessel at a temperature between about 20 kPaa to about 50 kPaa.

In another optional aspect, the method includes providing the tailings solvent recovery vessel with a downward solvent recovered tailings fluid velocity between about 0.07 m/s and about 0.2 m/s.

In another optional aspect, the method includes providing the tailings solvent recovery vessel with a retention time between about 5 minutes and about 1 minute.

In another optional aspect, the method includes providing the tailings solvent recovery vessel with a retention time between about 2 minutes and about 1 minute.

DETAILED DESCRIPTION

According to an embodiment of the present invention, the process and unit allow improved control of feed flow and temperature that set the enthalpy input to the flash column, thereby achieving high solvent recoveries.

Figure 1:
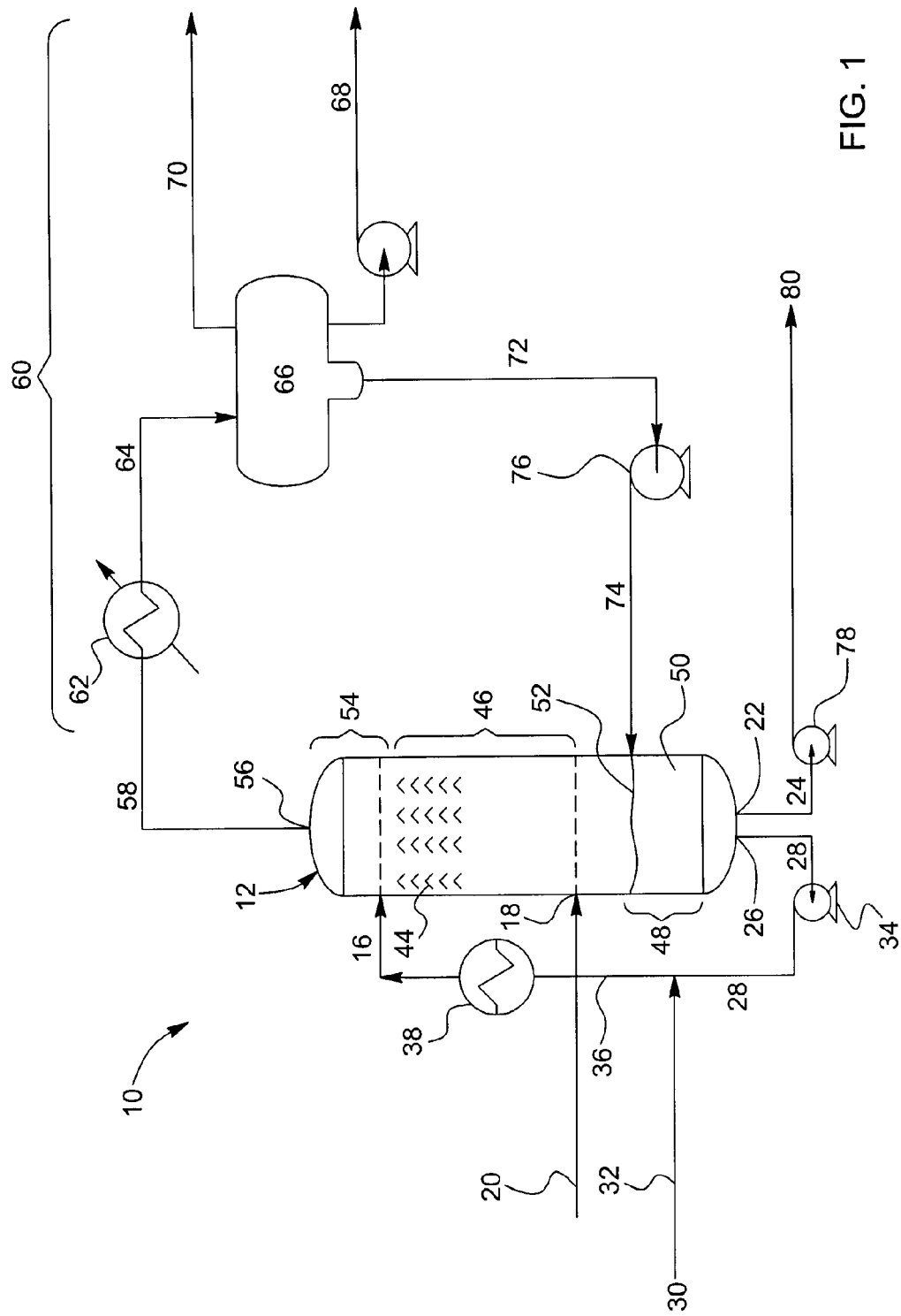
FIG. 1 is a block flow diagram of a tailings solvent recovery unit or a single stage of a tailings solvent recovery unit, according to an embodiment of the present invention.

Referring to FIG. 1, illustrating an embodiment of the present invention, a tailings solvent recovery unit 10 is provided and comprises at least one tailings stripping column 12 having a tailings inlet for providing the tailings feed 16, a steam inlet 18 for providing steam 20, a solvent recovered tailings outlet 22 for withdrawing a portion 24 of the solvent recovered tailings for further treatment or processing, and a recycle outlet 26 for recycling recycled solvent recovered tailings portion 28 of the bottoms.

Further upstream, froth treatment tailings 30 are provided to the tailings solvent recovery unit 10 via a froth treatment tailings line 32. The froth treatment tailings 30 are combined with the recycled solvent recovered tailings 28, which are supplied from the bottom of the stripping column by a recycle pump 34, to form a flow controlled froth treatment tailings feed 36. Depending on the relative flow rates of the froth treatment tailings 30 and the recycled solvent recovered tailings 28, the flow controlled froth treatment tailings feed 36 may be given a constant flow or a tailored flow for the stripping column for a given situation. In one aspect, the flow controlled froth treatment tailings feed 36 is supplied to a feed heat exchanger 38 which heats the tailings and provides the tailings feed 16 as a flow and temperature controlled tailings feed.

In one aspect, the tailings solvent recovery unit 10 preferably comprises a column bottoms pump-around system, which preferably comprises any lines, pumps, heat exchangers, mixing devices, and the like, to effect the bottoms recycle in controlling the flow and temperature of the tailings feed 16.

It should be noted that the recycled solvent recovered tailings may be added to froth treatment tailings using any number of fluid mixers or pipe intersections, including but not limited to T-junctions, angled-junctions, co-annular addition, in-line mixing equipment and the like, and may also include a mixing device, such as a static mixer, a flow restriction creating turbulence and the like, to enhance mixing of the streams to form a substantially homogeneous feed.

Flow rate control of the feed 16 is desirable for a number of reasons. Constant flow rate allows maintenance of pressure in the inlet line to accomplish a one-phase liquid feed, which is particularly desirable since in-line vapour flashing of solvent diluted tailings can cause the abrasive particulate solids within the tailings to be accelerated with the flashed vapour to high velocities resulting in intense wear and potentially severe damage to equipment. Maintaining the tailings feed in liquid phase can be done is several ways. Water may be added to the feed, but water addition is inefficient since water is a costly commodity and also must be heated prior to addition. The backpressure exerted on the feed could also be modified in response to fluctuations in feed flow rate to maintain adequate pressure to inhibit vapour flashing. However, the relationship between pressure drop ($\Delta P$) and flow rate (Q) is not linear but rather exponential ($\Delta P \, \alpha \, Q^2$) and, consequently, pressure regulation in response to variations in flow rate can require large pressure drop changes in response to even small changes in flow rate. The recirculation system described herein enables flow rate control to stabilize pressure and temperature.

The recirculation of a recycled solvent recovered tailings stream to supplement and control the tailings feed, has a number of advantages. First, it reuses part of a stream from the process, rather than requiring external input such as water. Second, it allows flow rate control of the feed, eliminating pressure drop control to maintain the feed in liquid phase prior to the stripping column. Third, when the tailings feed supply decreases, due to upstream shutdown or modifications in the bitumen froth separation operation, the TSRU circuit can continue circulating. In some cases, a valve upstream of the addition point of the recycled solvent recovered tailings can be closed and the recirculation may be fully engaged. This type of downtime operational flexibility has the advantage of reducing fouling in the equipment due to asphaltenes and minerals from sitting in pipework and equipment while the upstream operations are off line or corrected. Fourth, the TSRU can operate independently of upstream and downstream units, which can shut down while the TSRU continues to run a loop, which can advantageously be run to maintain adequately high temperatures. In this regard, it is also noted that the most significant losses of solvent occur during start-up and shut down. The recirculation maintains the TSRU system running and thus avoids costly solvent loss. It is also noted that the first and second stripping columns can each have their own recirculation system, such that if the first column goes off-line, the second column underflow can be recirculated to continue circulation through the second stage. More regarding the various embodiments, variants and preferred aspects of the recirculation system will be further described herein below with reference to the Figs.

The combining of the froth treatment tailings 30 and the recycled solvent recovered tailings 28 may be performed by various means and methods. For instance, the streams may flow into each other via a tee junction or another type of pipeline junction at an angle other than 90°. There may be one or more supplementary mixer in between addition point and the heat exchanger or another appropriate location near the tee junction or after the heat exchanger, as the case may be. The streams may be added together in a mixer or blending apparatus, which may be in-line or otherwise configured. The mixer may be configured to impart sufficient amounts of shear mixing to the streams in order to achieve a desired mixing level or homogeneity in a given time interval or pipeline distance. In one aspect, the mixing shear imparted to the streams may be sufficient to encourage breakup of the hydrocarbon structure for release of solvent. Allowing break up of the hydrocarbon structure into smaller drops and breakup of flocs increases the surface area and, in turn, improves solvent release performance. The mixing means could also include the pipe inlet configuration and fittings, with sufficient pipe length, elbows, bends, valves and the like to achieve the desired level of shear prior to introduction into the flash or stripping column 12.

Referring still to FIG. 1, the tailings stripping column 12 may also have shed decks 44 or other types of internals arranged within it.

In one optional aspect, the tailings stripping column 12 has a stripping section 46 for accommodating stripping of the solvent from the solvent diluted tailings and a bottom section 48 for accumulation of the solvent recovered tailings component, which may form a liquid pool 50 having an upper surface 52. The tailings stripping column 12 may be operated so as to maintain a relatively constant liquid level of the pool, for instance using level control associated with the outlet pumps. More regarding the level of the pool in relation to streams entering the stripping column will be discussed herein below. The tailings stripping column 12 may also be operated so as to provide a down velocity and retention time for the liquid pool sufficient to reduce or minimize separation of the hydrocarbon phases from the aqueous phases within the pool. Typical down velocities may be selected above about 0.07 m/s and preferably above about 0.1 m/s. Retention time provides a working volume for the pumps. In some aspects, the retention time may range up to about 5 minutes or in the range of about 1 to 2 minutes. It should nevertheless be noted that the above values for down velocity and retention time preferably apply to normal operating conditions of the TSRU and may be modified during other operational modes. It is also noted that retention times for the solvent diluted tailings may remain relatively constant in different operational modes and are provided mainly based on volumes required to operate and control upstream and downstream equipment. On the other hand, the residence time is enhanced by the recirculation system, as each amount solvent diluted tailings that enters the solvent recovery unit remains in circulation for a greater period of time for smaller vessel sizes, thereby increasing the solvent recovery performance for smaller and thus less costly equipment.

The tailings stripping column 12 also has an upper section 54 having an overhead outlet 56 for releasing vaporised solvent 58.

Referring still to FIG. 1, the tailings solvent recovery unit also includes an overhead system 60 that receives vaporised solvent 58 from the upper section 54 of the tailings stripping column 12. The overhead system 60 separates the vaporised solvent 58 into various streams that can be recycled, recovered or disposed of. In one aspect, the overhead system 60 comprises an overhead condenser 62 for condensing the vaporised solvent 58 and producing a condensed solvent 64. The condensed solvent 64 can then be supplied to an overhead separator 66, which separates it into recovered solvent 68, vent gas 70 and produced water 72. The produced water 72 may be reused in the tailings treatment process, for example by recycling at least a portion of it as recycled water 74 back into the tailings stripping column 12 using a water recycled pump 76. In one aspect, some or all of the produced water could also be routed directly to feed or water treatment for recycled and reuse. In another aspect, the withdrawal of the vent gas 62 controls the separator pressure, which may preferably be atmospheric or vacuum with the vent gas 62 further treated as required by plant emission regulations.

The various inlet and outlet streams of the tailings stripping column 12 are preferably arranged with respect to teach other and certain parameters of the column itself. For instance, in one aspect, the recycled water 74 is input at or near or preferably below the upper surface 52 of the liquid pool 50; the steam 20 is injected above the recycled water 74. In one aspect, the recycled water 74 is input below the upper surface 52 of the liquid pool 50 to ensure proper suction and liquid phase flow from the overhead separator 66. More regarding the relative arrangement of the inlet and outlet streams will be discussed in relation to the illustrated embodiments of FIGS. 2 and 3 further below.

Referring still to FIG. 1, the portion 24 of solvent recovered tailings that is not recycled is preferably pumped using column tailings pump 78 to tailings disposal or further processing, further treatment units, or as first stage tailings 80 to a second stage stripping column. Further processing may include water, mineral or hydrocarbon recovery processes, or a combination thereof. More regarding multi-stage stripping of the tailings will be discussed further below in reference to FIGS. 2 and 3.

Figure 2:
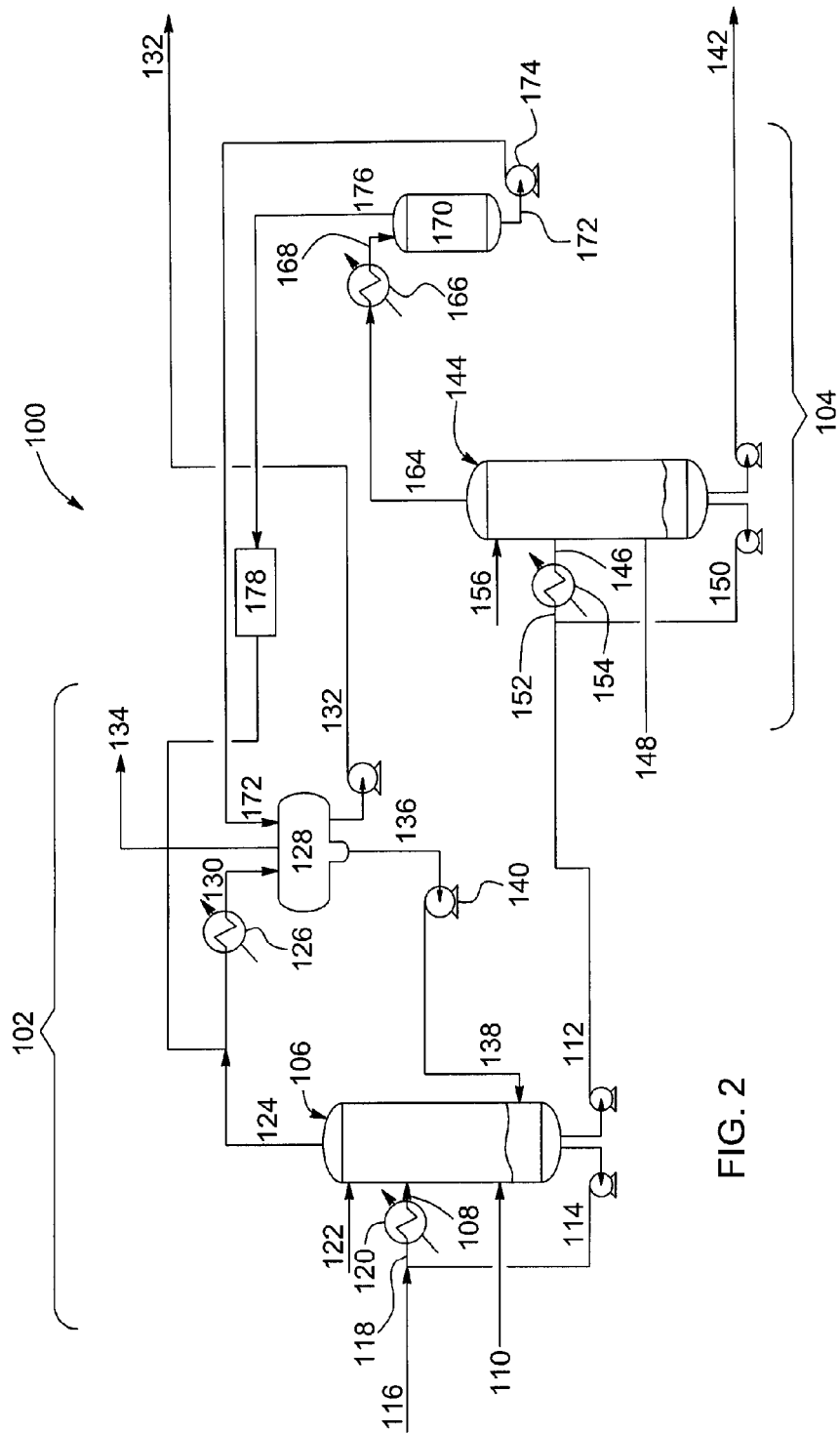
FIG. 2 is a block flow diagram of a two-stage tailings solvent recovery unit according to an embodiment of the present invention.
Figure 3:
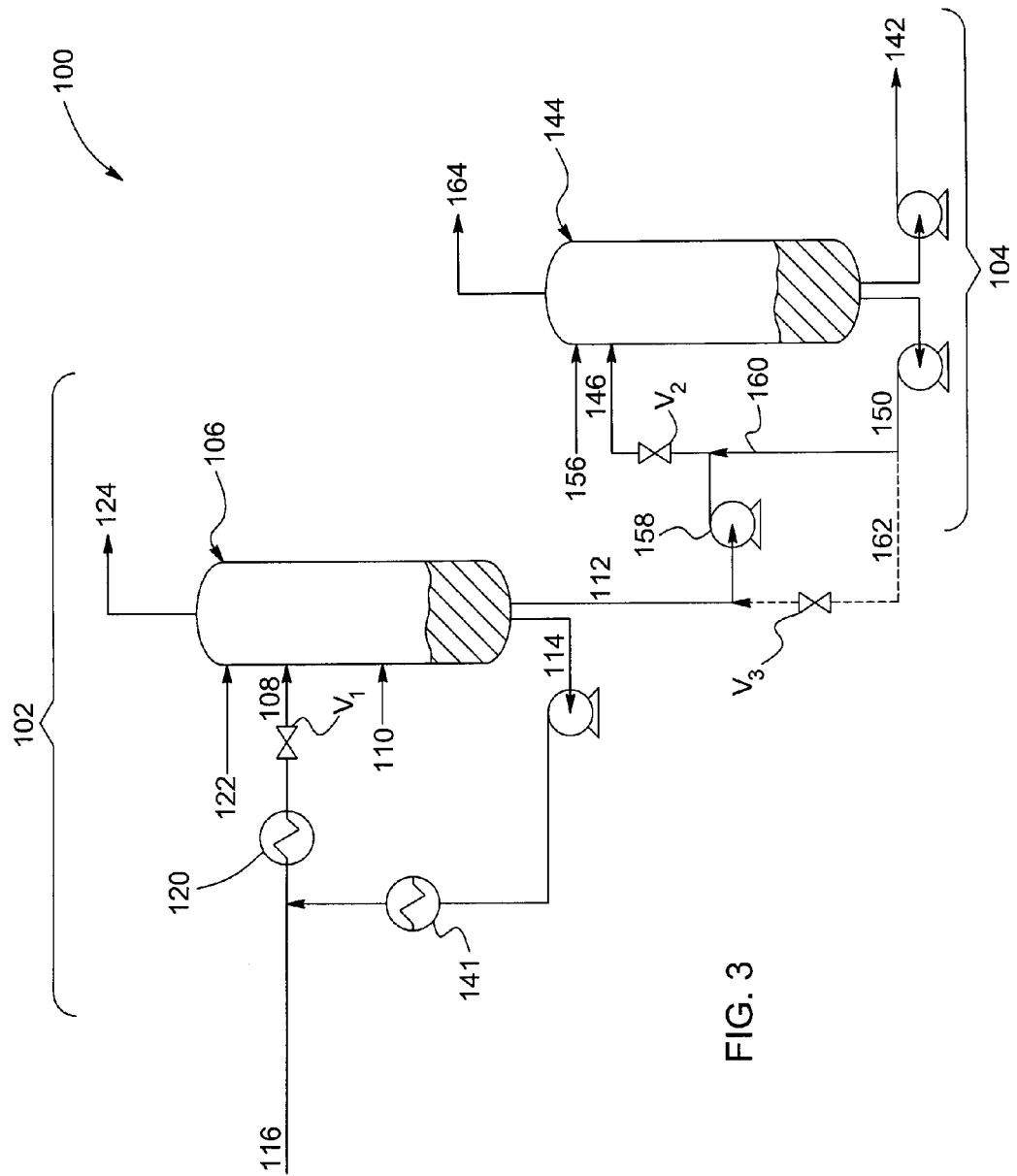
FIG. 3 is a block flow diagram of a two-stage tailings solvent recovery unit according to another embodiment of the present invention.

FIG. 2 provides a relatively detailed illustration of a two-stage tailings recovery process and unit, according to an embodiment of the present invention, although some equipment and components such as pumps, valves and control devices are not illustrated. FIG. 3 shows a less detailed process and unit, notably without an overhead system.

Referring to FIGS. 2 and 3, the two-stage tailings recovery unit 100 comprises a first stage 102 and a second stage 104. It will be understood that the first and second stages can have various levels of integration and recycling with each other, some of which is illustrated. It will be understood that in other embodiments there may be more than two stages, depending on column sizing, stream compositions and processing parameters, such as configuring the two-stage tailings recovery unit 100 to either treat froth treatment tailings from one or more froth treatment plants in a single unit or using multiple units in parallel.

As shown in FIGS. 2 and 3, a first stripping column 106 receives a tailings feed 108 and optionally steam 110 for stripping the tailings within the column to produce first stage tailings 112 and first stage recycled tailings 114. The first stage recycled tailings 114 are circulated back as feed to the first column 106. As illustrated, the first stage recycled tailings 114 are added to froth treatment tailings 116 to produce a combined stream, preferably in a manner so as to control the flow rate of the feed and thus produce a flow controlled froth treatment tailings feed 118. The flow controlled froth treatment tailings feed 118 may undergo a heat treatment in a first stage heat exchanger 120 in order to produce the tailings feed 108 as a flow and temperature controlled tailings feed. It should also be noted that the first stage recycled tailings 114 may be partially added to the froth treatment tailings 116 and partially returned directly into the column 106 as an intermediate returned tailings (not illustrated). There may also be a defoaming agent 122 supplied to the upper section of the column 106, optionally via a spray system for distribution into the column.

Referring now to FIG. 2 only, the first stage 102 also includes an overhead system coupled to the first stage flash column 106 to receive and process vaporized solvent 124. In one embodiment, the overhead system may include a condenser 126 and separator 128 in series. The vaporized solvent 124 may be condensed by the condenser 126 and the resulting condensed solvent 130 supplied to the first stage separator 128. The first stage separator 128 receives at least the condensed solvent 130 and produces first stage recovered solvent 132, first stage vent gas 134 and first stage produced water 136.

At least a portion of the first stage produced water 136 may be returned to the first stage column 106 as first stage recycled water 138. The first stage recycled water 138 is preferably pumped by a water pump 140 to below the upper surface of the pool in the first stage column 106 or alternately (not shown) below the upper surface of the pool in the second stage column 144.

Referring to FIG. 2, the first stage 102 may also have a recycle heat exchanger 141 for heating the first stage recycled tailings 114 prior to addition to the froth treatment tailings 116. The recycle heat exchanger 141 may bring the first stage recycled tailings 114 to a same or similar temperature as the froth treatment tailings 116. The recycle heat exchanger 141 may also be sized smaller than the main feed first stage heat exchanger 120, since it is heating a lower flow rate of material.

Referring to FIGS. 2 and 3, in the two-stage unit 100, the first stage tailings 112 are provided as feed for the second stage 104. A large part of the second stage 104 may be configured similarly to the first stage 102, with various recycle streams and heating equipment being provided and managed in accordance with the second stage operating conditions. However, there are some preferred operational differences, including the first stage stripping column operating at or above atmospheric pressure and the second stage stripping column operating at vacuum pressures. It will also be understood particularly from FIG. 2 and the below description, that the second stage is preferably integrated with the first stage to have several different configurations to enhance the overall solvent recovery process. It should be noted that there may optionally be three or more stages arranged so that each subsequent stage receives at least part of the tailings from the previous column, or arranged in parallel with integrated fluid interconnections between various equipment.

Referring to the embodiment in FIG. 2, it will be noted that the first stage recovered solvent 132 and the vent gas 134 are the only streams recovered from the first stage 102 and that end-product tailings 142 is the only stream expelled from the second stage 104, with the other streams being recycled back into the system.

More particularly, as shown in FIGS. 2 and 3, the second stage 104 comprises a second stage stripping column 144, which receives a second tailings feed 146 and optionally steam 148 for stripping the tailings within the column 144 to produce second stage tailings. The second stage stripping column may produce only one tailings stream as end-produce tailings, but it may optionally be configured to produce two separate streams as described hereafter. The second stage stripping column may produce second stage tailings 142 as end-product tailings as well as second stage recycled tailings 150. The second stage recycled tailings 150 are circulated back as feed to the second column 144.

As illustrated in FIG. 2, the second stage recycled tailings 150 are added to first stage tailings 112 to produce a combined stream, preferably in a manner so as to control the flow rate of the feed and thus produce a flow controlled second tailings feed 152. The flow controlled second tailings feed 152 may undergo a heat treatment in a second stage heat exchanger 154 in order to produce the second tailings feed 146 as a flow and temperature controlled second tailings feed. It should also be noted that the second stage recycled tailings 150 may be partially added to the first stage tailings 112 and partially returned directly into the second column 144 as an intermediate returned tailings (not illustrated) or into another stream (not illustrated). There may also be a defoaming agent 156 supplied to the upper section of the second column 144, optionally via a spray system (not illustrated) for distribution into the column 144.

Referring now to FIG. 3, the second stage 104 may be provided with various recycle line configurations in order to enhance performance and afford flexible operation. In one aspect, if the first stage is brought off-line or experiences operational problems, the second stage can be operated on a closed loop by recirculation of the underflow tailings from the second stripping column back for re-feeding the second stripping column. The recirculation system may have several configurations. As illustrated, the recirculation system may recirculate the second stage recycled tailings 150 downstream of a first column tailings pump 158 through recycle line 160 or upstream of the first column tailings pump 158 through recycle line 162.

As noted above, the first column 106 is operated at or above atmospheric pressure while the second column is operated at vacuum pressure.

Turning now to FIG. 3, the recirculation and feed systems of the first and second columns may advantageous include various valves, backpressure devices or a combination thereof. In one aspect, there is a valve $V_1$ provided for first stage column feed. The valve $V_1$ provides sufficient backpressure on the froth treatment tailings 116 to maintain a liquid phase flow.

Still referring to FIG. 3, the recirculation and feed system may comprise recirculation valves $V_2$ or $V_3$ or both, as the case may be. Of course, there may be additional valves for controlling the recirculation and feed system.

Regarding placement of the valves with respect to other system components, it is preferred that valves $V_1$, $V_2$ and $V_3$ are located to control upstream phase separation. $V_1$ is preferably located downstream of the heat exchanger 120 to minimize flashing risk in the heat exchanger 120. $V_2$ is preferably located just upstream of the second column 144 to control phase separation. $V_3$ is preferably located as illustrated to allow recycle to maintain first stage U/G in standby mode. It should nevertheless be noted that the valves may have other configuration and locations depending on the specific setup of the overall system. There may also be additional valves to enable various variants of the process, as the case may be.

Referring to FIG. 2, the second stage 104 also includes an overhead system for treating second vaporized solvent 164 released from the second stripping column 144. The overhead system includes a second condenser 166 for producing a condensed solvent 168 which is then supplied to a second stage knock-out drum 170. The second stage knock-out drum 170 produces second stage condensate 172 which may be pumped by condensate pump 174 back to the first stage separator 128. The second stage knock-out drum 170 also produces drum vapour 176 which may be supplied back to mix with the first stage vaporized solvent 124 by means of a vacuum package 178. The vacuum package 178 may comprise steam ejection or vacuum pumps or a combination thereof. In addition, with optional heating (not illustrated), the degree of vacuum versus the heat input may be coordinated and optimized.

Embodiments of the present invention enable various advantages. In one aspect, recycle of stripped column tailings can reduce or eliminate the need for addition fluids to maintain optimum feed flows to the column. The recycle pump, which preferably has variable speed capabilities, may be operated to control either feed pressure or total feed flow at a value that is set, pre-determined, calculated, or continuously or periodically updated. In one optional aspect, the recycle pumps may be configured in each stage to share common spare pumps (not illustrated) with other pumps such as the treated tailings pump. This option allows cost savings for pumps while enabling pump backup for increased security and flexibility for the process. In another optional aspect, valve control with advanced abrasion restraint materials could be used to control the recirculation flow. In another aspect, the column bottoms stream is at equilibrium temperature and pressure and recycling this stream during reduced flows can minimize heat input. In another aspect, a feed heater is arranged to heat either the combined tailings stream 36 or the recycle stream 28 prior to mixing with froth treatment tailings 30, or a combination thereof. The heater may be a conventional heat exchanger, or a spiral heat exchanger or a direct steam injection heating device with a requirement that the heater is specified to minimize erosion and plugging from solids (mineral or bitumen or both) present in the stream. In another aspect, controlling of feed to the tailings stripping column by recycling stripped column tailings maintains a constant liquid loading and distribution of feed to column internals. In another aspect, controlling the feed temperature either by heating the recycled stripped column tailings or blended fresh tailings with recycled tailings permits consistent column operations to optimize diluent recovery. The control method may apply to paraffinic or naphthenic froth treatment processes as variations may originate in the upstream froth treatment plant. The control method while identified for a single stage flash column can apply to columns in series or parallel operation. In another aspect, the recycle and heating of stripped tailings also allows start-up and shut down operations separate from the froth treatment plant, for example allowing the TSRU to change to standby mode in which cold process water could be added to stripped tailings 142 to maintain line velocities and appropriate densities, if going to tailings, without heating costs.

In one embodiment, stripped column tailings are recycled to the stripping column feed to maintain a constant feed pressure as shown on the flow diagrams or alternately flow control could be used. The feed heater may trim the feed temperature to a set pressure, mitigating temperature variation due to froth treatment tailings feed and slops variations.

In one embodiment, the recycle pump and associated pipes and controls allow for recirculation of stripped tailings and maintenance of a constant and reliable column feed.

In one embodiment, the feed heater is beneficial for varying feed temperature. It may be preferable to have a heater at the first stage stripping column while the second stage column may be operated without a recycle system heater, as the temperature variation in the second stage may be limited and not warrant installing a second heater.

In one preferred operation of the tailings solvent recovery unit, in the tailings stripping column feed is distributed over internals, optionally in contact with stripping steam, and flashes into a vapor stream that reports to the overhead condensing system while stripped tailings are collected in the bottom of the column. The overhead vapors are cooled by a condenser and separated into a vent gas stream, a solvent stream and a produced water stream by a three-phase separator. Note that the solvent is immiscible with water and separates by gravity in the separator. Regulation of the vent gas stream preferably controls the pressure in the overhead separator which, in turn, by pressure loss across the condenser sets the column pressure at which the solvent flashes. The produced water is potentially contaminated by entrained hydrocarbons and particulate material and is thus preferably blended into stripped tailings, for instance into the pool in the column or to the tailings pipeline upstream or downstream of the pump. Alternately, produced water which is primarily condensate can be treated by conventional water treatment methods for recycle. The recovered solvent is recycled to the froth treatment plant as solvent for addition to bitumen froth. A portion of stripped tailings are recycled to the column feed by speed control of the recycle pump with the remainder forwarded by speed control of the column tailings pump to subsequent process operations. The column tailings pump preferably maintains the level of stripped tailings in the column to provide adequate suction conditions for both bottoms pumps. In one aspect, the abrasive and segregating nature of tailings streams is mitigated by flow management using two separate pumps. It should nevertheless be understood that various configurations and resistant materials could be used in association with a single pump to perform the required flow management.

In another embodiment, the recovery of solvent from froth treatment tailings helps meet environment discharge requirements and incremental solvent recovered increases bottom line revenue in the overall process.

It is noted that the above description and FIGS. 1-3 are with respect to the preferred embodiment of recovering a paraffinic solvent from tailings that have been derived from a paraffinic froth treatment (PFT) process.

In another optimal embodiment, the solvent or diluent recovered is naphtha as used in a naphthenic froth treatment processes. While units for recovering naphtha from froth treatment tailings are generally referred to as naphtha recovery units (NRUs), it should be understood that the term "tailings solvent recovery unit" (TSRU) as described and used herein may refer to recovering either paraffinic or naphthenic solvents from tailings.

It should be noted that a difference between the paraffinic and naphthenic embodiments is operating envelopes and configurations comprising temperature, pressure and number of stages to achieve diluent recoveries as constrained by reasonable column velocities due to the flashing of water with the diluent. These operating envelopes and configurations predominately reflect the diluent properties. With low boiling diluents such as paraffinic embodiments, the recirculation system provides consistent feed pressures to the column and liquid flows within the column that inhibit depositions and or accumulations of asphaltenes or minerals. With high boiling diluents such as in naphthenic embodiments, the recirculation system coupled with the optional pre-heating embodiments permit stabilizing column operation at pressures and temperatures without excessive evolution of water vapor to the column overhead system.

In the naphthenic embodiment, the recovery of naphtha without asphaltenes precipitated in froth treatment tailings is facilitated by employing one or more stages with feed from the froth treatment plant at about 65° C. to about 85° C., and generally about 80° C., and flashed about 20 kPaa to about 50 kPaa, typically about 28 kPaa with stripping steam aiding stripping naphtha from the tailings. The recycle of stripped tailings and heater as disclosed herein permits stable column operation to maximize recovery of naphtha.

In the paraffinic embodiment, the paraffinic solvent diluted tailings to be treated comprise precipitated asphaltenes and solvent which is partially entrapped by asphaltene-bitumen matrices. There are various challenges to removing the paraffinic solvent from the asphaltene-bitumen matrices. Not all paraffins have the same diffusivity and mobility in the matrices. Paraffinic solvents comprising branched isomers, such as iso-butane, iso-pentane or iso-hexane, have lower diffusivities in asphaltene-bitumen matrices present in the solvent diluted tailings and thus are more difficult to release from the matrices for solvent recovery. Some work has been done to determine paraffin diffusivities, for instance Fu & Phillips' "*New technique for determination of diffusivities of volatile hydrocarbons in semi-solid bitumen*", Fuel, 1979, Vol. 58, August, pages 557-560. For example, according to Fu & Phillips i-hexane has a diffusivity about 30% lower than n-hexane in a semi-solid Athabasca bitumen sample. Some PFT processes employ a mixture of iso- and normal-paraffins to separate the bitumen froth into high diluted bitumen and underflow asphaltene-containing tailings. Mixtures of i-butane and n-butane, i-pentane and n-pentane or i-hexane and n-hexane are in fact often used due to availability and cost of such mixtures. However, the iso-paraffins may preferentially be retained within the asphaltene-bitumen matrices in the tailings streams due to lower diffusivity. Cyclic hydrocarbons also tend to have lower diffusivities and are more difficult to remove from asphaltene-bitumen matrices. The heavy-hydrocarbon component in the solvent dilute tailings fed to the paraffinic TSRU is relatively high, especially compared to naphthenic-based processes, which directionally increases the thickness though which paraffinic solvent needs to diffuse. Asphaltenes also have a relatively low mobility compared to other heavy hydrocarbon components.

As a result of the higher asphaltene content in paraffinic froth treatment tailings, recovery of paraffinic solvent is particularly facilitated by employing two or more stages. To permit the froth treatment process temperature to vary as required to achieve the deasphalted bitumen product, the recycle and heating of stripped $1^{st}$ stage tailings 28 maintains a consistent $1^{st}$ stage column feed temperature of between about 70° C. and about 90° C., typically about 90° C., or above the highest froth treatment process temperature. The condensation conditions in the overhead systems maintain the $1^{st}$ stage column between about 100 kPaa and about 250 kPaa, typically about 224 kPaa, and the $2^{nd}$ stage column between about 20 kPaa and about 100 kPaa, typically about 68 kPaa, to maximize solvent recovery. It should be noted that the pressures and temperatures in the system may be varied and coordinated within an operating envelope to achieve desired operational performance. In addition, measures to prevent aggregation of the asphaltene-bitumen matrix are facilitated by maintenance of constant flow rates, minimum retention times, and continuous operability during upstream or downstream outages or downtimes also contribute to solvent recovery.

In one aspect, the TSRU equipment is designed, sized and configured such that the recirculation system can adapt to variations in solvent diluted tailings flow rates of up to 10%, 20%, 30%, 40% or even 50%. In this regard, design considerations include requirements for pumping, pressure drops, operating conditions such at temperature and avoiding settling in the particulate containing slurry streams.

Some optional aspects of the process of the present invention may be used to increase solvent recovery:
Management of the temperature and pressure in the stripping column along with the feed flow rate, to control stripping column vapour velocities and limit water boiling to maximize solvent recovery and minimize mineral carryover into overhead systems.
In startup mode, recirculation of a startup amount of initially cold tailings through the stripping column while heating through the recirculation feed line permits commissioning and decommissioning of the froth treatment tailings unit independently from upstream processes and minimizing diluent losses on unit startup.

The following provides some definitions and additional description for streams and equipment mentioned in the present specification:
Bitumen is viscous petroleum with a density similar to water and by solubility classification bitumen dissolves in aromatic solvents and precipitates asphaltenes in alkane (paraffinic) solvents. The fraction of bitumen soluble in paraffinic solvents is referred to as maltenes. Bitumen quality and properties vary depending on various factors including the origin of the formation, reservoir or ore body from which it is derived. For example while Athabasca bitumen has an asphaltene content of about 16 wt % to about 21 wt %, diluents used in froth treatment can increase the asphaltene content in the bitumen reporting to the tailings stream.
Diluent is a solvent which by solubility classification ranges from paraffinic to aromatic or blends of both and by vapour-liquid equilibrium can be separated from bitumen by steam or gas stripping methods. In froth treatment, diluent is added to bitumen froth to reduce both the viscosity and the hydrocarbon density for the physical separation of hydrocarbon phase from water or asphaltene phases, or both, using gravity or accelerated gravity methods.
A flash column may be referenced as a column, a column vessel, a vessel, a stripping column in the case where steam is injected, or similar terms. In all cases, the column is a pressure vessel rated for atmospheric or sub-atmospheric operations involved in the specific flash separation.
A recycle system may be referenced to as a pump-around system, bottoms recycle system, bottoms recirculation, tailings recycle or similar terms. The terms may also apply the components in the recycle system: pumps, lines, heaters, etc.

It is also noted that the heating of the various recycle and feed streams may be performed by a number of heater devices, such as indirect heat exchangers to recover heat from other process streams, heat exchangers receive heat from steam, or direct steam injection devices.

The invention claimed is:

1. A tailings solvent recovery process for recovering a solvent from a feed of solvent diluted tailings derived from a bitumen froth treatment operation, the feed having a variable flow, the process comprising:
supplying the feed to a tailings solvent recovery vessel and introducing the feed therein;
separating the solvent diluted tailings to produce a recovered solvent component and a solvent recovered tailings component;
discharging the solvent recovered tailings component from the tailings solvent recovery vessel as a discharged solvent recovered tailings component;
recycling a portion of the solvent recovered tailings component as a recycled tailings component back into the feed to produce a flow rate controlled feed that is introduced into the tailings solvent recovery vessel.

2. The process of claim 1, wherein the separating of the solvent diluted tailings comprises stripping.

3. The process of claim 1, comprising feed heating the flow rate controlled feed to a controlled inlet temperature for the separating.

4. The process of claim 3, wherein the feed heating is performed to promote a constant feed temperature for the separating.

5. The process of claim 1, comprising heating the recycled tailings component prior to introduction into the feed of the solvent diluted tailings.

6. The process of claim 5, wherein the recycle heating is performed to promote a constant feed temperature for the separating.

7. The process of claim 1, wherein the recovered solvent component comprises a vaporized solvent, and the process further comprises condensing the vaporized solvent to produce a condensed solvent.

8. The process of claim 7, comprising separating the condensed solvent into vapour, purified recovered solvent and produced water.

9. The process of claim 8, comprising recycling at least a portion of the produced water back into the separating of the solvent diluted tailings.

10. The process of claim 9, wherein the recycling of the produced water is performed below a liquid level of a pool of the solvent recovered tailings component.

11. The process of claim 1, wherein recycling of the recycled tailings component is performed at a ratio of the recycled tailings component to the solvent recovered tailings component of between about 50% and about 200% in standard operating mode.

12. The process of claim 1, wherein recycling of the recycled tailings component is performed at a ratio of the recycled tailings component to the solvent recovered tailings component of between about 80% and about 120% in standby operating mode.

13. The process of claim 1, wherein the separating comprises stripping which comprises a first stripping stage and a second stripping stage arranged in series, the first stripping stage producing a first solvent recovered tailings component comprising residual solvent, the second stripping stage receiving the first solvent recovered tailings and producing a second solvent recovered tailings component and a second vaporized solvent.

14. The process of claim 13, comprising heating the first solvent recovered tailings component prior to introduction into the second stripping stage.

15. The process of claim 13, comprising recycling a portion of the second solvent recovered tailings as a second recycled tailings component into the first solvent recovered tailings to produce a flow rate controlled second feed for introduction into the second stripping stage.

16. The process of claim 15, comprising heating the flow rate controlled second feed to a controlled inlet temperature for the second stripping stage.

17. The process of claim 16, wherein the heating of the flow rate controlled second feed is performed to promote a constant second feed temperature into the second stripping stage.

18. The process of claim 15, comprising heating the second recycled tailings component prior to introduction into the first solvent recovered tailings.

19. The process of claim 13, comprising condensing the second vaporized solvent to produce a second condensed solvent, and separating the second condensed solvent into a separated solvent component containing residual water and a vapour component.

20. The process of claim 19, wherein the separating of the second condensed solvent is performed in a knock-out drum.

21. The process of claim 19, comprising recycling the vapour component back into the solvent component released from the first stripping stage.

22. The process of claim 21, wherein the recycling of the vapour component is aided by a vacuum package.

23. The process of claim 19, comprising recycling at least a portion of the separated solvent component back for separation with the condensed solvent.

24. The process of claim 23, comprising recycling all of the separated solvent component back for separation with the condensed solvent.

25. The process of claim 1, wherein the solvent is a paraffin derived from a paraffinic bitumen froth treatment process.

26. The process of claim 1, wherein the solvent is naphtha derived from a naphthenic bitumen froth treatment process.

27. The process of claim 1, wherein the recycling of the recycled tailings component back into the feed of the solvent diluted tailings is performed:
to allow sufficient pressure on the flow rate controlled feed to avoid vapour flashing prior to the tailings solvent recovery vessel.

28. The process of claim 27, comprising moderating the temperature of the flow rate controlled feed to produce a flow rate and temperature controlled feed.

29. The process of claim 27, wherein the tailings solvent recovery vessel comprises a stripping column.

30. The process of claim 27, wherein the tailings solvent recovery vessel comprises a plurality of stripping columns arranged in series.

31. The process of claim 27, comprising applying the pressure on the flow rate controlled feed via a valve device.

32. The process of claim 27, comprising applying the pressure on the flow rate controlled feed via a flow restriction.

33. The process of claim 27, comprising pre-heating the recycled tailings component prior to introduction into the feed of the solvent diluted tailings.

34. The process of claim 27, comprising pre-heating the flow rate controlled feed using a heat exchanger.

35. The process of claim 27, comprising:
releasing solvent vapour from the tailings solvent recovery vessel;
recovering produced water from the solvent vapour; and returning the produced water back into the tailings solvent recovery vessel.

36. The process of claim 35, wherein the produced water is returned into a pool of accumulated solvent recovered tailings in the tailings solvent recovery vessel.

37. The process of claim 27, wherein the solvent is a paraffinic solvent and the solvent diluted tailings are derived from a paraffinic bitumen froth treatment process.

38. The process of claim 37, wherein the tailings solvent recovery vessel comprises a first stage column fed at a temperature of between about 70° C. and about 90° C.

39. The process of claim 38, wherein the first stage column is fed at a temperature above a highest froth treatment process temperature.

40. The process of claim 38, wherein the tailings solvent recovery vessel comprises a second stage column operated between about 20 kPaa and about 100 kPaa.

41. The process of claim 38, wherein the paraffinic solvent comprises preferentially retained paraffins that are preferentially retained within asphaltene-bitumen matrices with respect other paraffins of the solvent due to lower diffusivity, and the process comprises providing a residence time of the solvent diluted tailings in the solvent recovery vessel to promote recovery of the preferentially retained paraffins.

42. The process of claim 41, wherein the preferentially retained paraffins comprise iso-paraffins.

43. The process of claim 27, wherein the solvent is naphtha and the solvent diluted tailings are derived from a naphthenic bitumen froth treatment process.

44. The process of claim 43, comprising operating the solvent recovery vessel at a temperature between about 65° C. and about 85° C.

45. The process of claim 43, comprising operating the solvent recovery vessel at a temperature between about 20 kPaa to about 50 kPaa.

46. The process of claim 27, comprising providing the tailings solvent recovery vessel with a downward solvent recovered tailings fluid velocity between about 0.07 m/s and about 0.2 m/s.

47. The process of claim 27, comprising providing the tailings solvent recovery vessel with a retention time between about 5 minutes and about 1 minute.

48. The process of claim 27, comprising providing the tailings solvent recovery vessel with a retention time between about 2 minutes and about 1 minute.

49. The process of claim 1, wherein a tailings solvent recovery unit (TSRU) is used for recovering the solvent from the solvent diluted tailings, the TSRU comprising:
a separation apparatus for receiving the solvent diluted tailings and producing the solvent component and the solvent recovered tailings component, the separation apparatus comprising:
the tailings solvent recovery vessel comprising a solvent removal section for accommodation removal of the solvent from the solvent diluted tailings and a bottom section for accumulation of the solvent recovered tailings component;
a tailings outlet for releasing the solvent recovered tailings component from the vessel;
a solvent outlet for releasing the solvent component from the vessel as a vaporized solvent;
a tailings inlet for supplying the feed to the vessel;
a tailings recycle line in fluid connection with the tailings inlet for recycling the portion of the solvent recovered tailings component as the recycled tailings component into the feed to produce the flow rate controlled feed for introduction into the vessel.

50. The process of claim 49, wherein the separation apparatus is a stripping apparatus, the vessel is a stripping vessel and the solvent removal section is a stripping section, the separation apparatus comprising a stripping fluid inlet for providing a stripping fluid to the stripping vessel to facilitate separation of the solvent component from the solvent recovered tailings component.

51. The process of claim 50, wherein the TSRU comprises a feed heat exchanger associated with the tailings inlet for heating the flow rate controlled feed to a controlled inlet temperature.

52. The process of claim 51, wherein the feed heat exchanger is configured to heat the flow rate controlled feed sufficiently to promote a constant feed temperature into the stripping vessel.

53. The process of claim 50, wherein the TSRU comprises a recycle heat exchanger associated with the tailings recycle line for heating the recycled tailings component prior to introduction into the feed of the solvent diluted tailings.

54. The process of claim 53, wherein the recycle heat exchanger is configured to heat the recycled tailings component sufficiently to promote a constant feed temperature into the stripping vessel.

55. The process of claim 50, wherein the TSRU comprises a condenser for receiving and condensing the vaporized solvent to produce a condensed solvent.

56. The process of claim 55, wherein the TSRU comprises a separator for receiving the condensed solvent and producing vapour, purified recovered solvent and produced water.

57. The process of claim 56, wherein the TSRU comprises at least one water recycle line for recycling at least a portion of the produced water back into the stripping vessel.

58. The process of claim 57, wherein the at least one water recycle line is fluidly connected to the stripping vessel below a liquid level of a pool of the solvent recovered tailings component in the stripping vessel.

59. The process of claim 50, wherein the tailings recycle line is configured and sized such that the ratio of the recycled tailings component to the solvent recovered tailings component is between about 50% and about 200% in standard operating mode.

60. The process of claim 50, wherein the tailings recycle line is configured and sized such that the ratio of the recycled tailings component to the solvent recovered tailings component is between about 80% and about 120% in standby operating mode.

61. The process of claim 50, wherein the stripping vessel is a first stripping vessel and the stripping apparatus further comprises a second stripping vessel arranged in series with the first stripping vessel, the first stripping vessel producing a first solvent recovered tailings component comprising residual solvent, the second stripping vessel receiving the first solvent recovered tailings and producing a second solvent recovered tailings component and a second vaporized solvent.

62. The process of claim 61, wherein the TSRU comprises a second tailings heat exchanger for heating the first solvent recovered tailings component prior to introduction into the second stripping vessel.

63. The process of claim 62, wherein the second stripping vessel comprises a second tailings recycle line for recycling a portion of the second solvent recovered tailings as a second recycled tailings component into the first solvent recovered tailings to produce a flow rate controlled second feed for introduction into the second stripping vessel.

64. The process of claim 63, wherein the TSRU comprises a second feed heat exchanger for heating the flow rate controlled second feed to a controlled inlet temperature.

65. The process of claim 64, wherein the second feed heat exchanger is configured to heat the flow rate controlled second feed sufficiently to promote a constant second feed temperature into the second stripping vessel.

66. The process of claim 63, wherein the TSRU comprises a second recycle heat exchanger for heating the second recycled tailings component prior to introduction into the first solvent recovered tailings.

67. The process of claim 61, wherein the TSRU comprises a second condenser for condensing the second vaporized solvent to produce a second condensed solvent, and a second separator for separating the second condensed solvent into a separated solvent component containing residual water and a vapour component.

68. The process of claim 67, wherein the second separator is a knock-out drum.

69. The process of claim 67, wherein the TSRU comprises a vapour recycle line for recycling the vapour component back into the solvent component released from the first stripping vessel.

70. The process of claim 69, wherein the vapour recycle line is associated with a vacuum package.

71. The process of claim 67, wherein the TSRU comprises a separated solvent recycle line for recycling at least a portion of the separated solvent component back into the first separator.

72. The process of claim 71, wherein the separated solvent recycle line is configured to recycle all of the separated solvent component back into the first separator.

73. The process of claim 49, wherein the solvent is a paraffin derived from a paraffinic bitumen froth treatment process.

74. The process of claim 49, wherein the solvent is naphtha derived from a naphthenic bitumen froth treatment process.

* * * * *